(12) United States Patent
Lee et al.

(10) Patent No.: US 7,615,067 B2
(45) Date of Patent: Nov. 10, 2009

(54) SURGICAL INSTRUMENT

(75) Inventors: Woojin Lee, Hopkinton, MA (US); Andres Chamorro, Natick, MA (US)

(73) Assignee: Cambridge Endoscopic Devices, Inc., Framingham, MA (US)

( * ) Notice: Subject to any disclaimer, the term of this patent is extended or adjusted under 35 U.S.C. 154(b) by 281 days.

(21) Appl. No.: 11/523,103

(22) Filed: Sep. 19, 2006

(65) Prior Publication Data

US 2007/0282371 A1 Dec. 6, 2007

Related U.S. Application Data

(60) Provisional application No. 60/811,046, filed on Jun. 5, 2006.

(51) Int. Cl.
*A61B 17/00* (2006.01)
(52) U.S. Cl. ...................... 606/205; 604/528
(58) Field of Classification Search ......... 606/139–146, 606/205–206; 604/528
See application file for complete search history.

(56) References Cited

U.S. PATENT DOCUMENTS

| | | | |
|---|---|---|---|
| 2,028,635 A | 1/1936 | Wappler | |
| 2,507,710 A | 5/1950 | Grosso | |
| 2,790,437 A | 4/1957 | Moore | |
| 3,107,954 A * | 10/1963 | Rudy | ............... 384/212 |
| 3,557,780 A | 1/1971 | Sato | |
| 3,858,577 A | 1/1975 | Bass et al. | |
| 3,895,636 A | 7/1975 | Schmidt | |
| 4,483,562 A | 11/1984 | Schoolman | |
| 4,688,554 A | 8/1987 | Habib | |

(Continued)

FOREIGN PATENT DOCUMENTS

EP 0 095 970 A2 12/1983

(Continued)

OTHER PUBLICATIONS

Nakamura et al., Multi-DOF Forceps Manipulator System for Laparoscopic Surgery—Mechanism Miniaturized & Evaluation of New Enterfaces, 5 pgs, Oct. 2001.

(Continued)

*Primary Examiner*—Todd E Manahan
*Assistant Examiner*—Eric Blatt
(74) *Attorney, Agent, or Firm*—David M. Driscoll, Esq.

(57) ABSTRACT

The surgical instrument includes a distal tool, a rigid or flexible elongated shaft that supports the distal tool, and a proximal handle or control member, where the tool and the handle are coupled to the respective distal and proximal ends of the elongated shaft via distal and proximal bendable motion members. Actuation means extends between said distal and proximal members whereby any deflection of said control handle with respect to said elongated instrument shaft causes a corresponding bending of said distal motion member for control of said working member. The proximal movable member comprises a movable ring assembly supported from the handle and adapted for three dimensional motion relative to the handle. A manually rotatable member may be arranged adjacent to the control handle for manually rotating the instrument shaft and working member relative to the control handle. A locking member may be supported from the control handle. The locking member is manually operable by a user and includes a follower the position of which is responsive to the position of the movable members.

42 Claims, 10 Drawing Sheets

U.S. PATENT DOCUMENTS

| | | | |
|---|---|---|---|
| 4,728,020 A | 3/1988 | Green et al. | |
| 4,763,669 A | 8/1988 | Jaeger | |
| 4,872,456 A | 10/1989 | Hasson | |
| 4,880,015 A | 11/1989 | Nierman | |
| 4,944,093 A | 7/1990 | Falk | |
| 4,944,741 A | 7/1990 | Hasson | |
| 4,945,920 A | 8/1990 | Clossick | |
| 5,002,543 A | 3/1991 | Bradshaw et al. | |
| 5,042,707 A | 8/1991 | Taheri | |
| 5,209,747 A | 5/1993 | Knoepfler | |
| 5,271,381 A | 12/1993 | Ailinger et al. | |
| 5,273,026 A | 12/1993 | Wilk | |
| 5,275,608 A | 1/1994 | Forman et al. | |
| 5,314,424 A | 5/1994 | Nicholas | |
| 5,330,502 A | 7/1994 | Hassler et al. | |
| 5,344,428 A | 9/1994 | Griffiths | |
| 5,383,880 A | 1/1995 | Hooven | |
| 5,386,818 A | 2/1995 | Schneebaum et al. | |
| 5,395,367 A | 3/1995 | Wilk | |
| 5,405,344 A | 4/1995 | Williamson et al. | |
| 5,433,721 A | 7/1995 | Hooven et al. | |
| 5,441,494 A | 8/1995 | Ortiz | |
| 5,454,827 A | 10/1995 | Aust et al. | |
| 5,501,654 A | 3/1996 | Failla et al. | |
| 5,520,678 A | 5/1996 | Heckele et al. | |
| 5,599,151 A | 2/1997 | Daum et al. | |
| 5,618,294 A | 4/1997 | Aust et al. | |
| 5,643,294 A | 7/1997 | Tovey et al. | |
| 5,702,408 A | 12/1997 | Wales et al. | |
| 5,759,151 A | 6/1998 | Sturges | |
| 5,766,196 A | 6/1998 | Griffiths | |
| 5,772,578 A | 6/1998 | Heimberger et al. | |
| 5,823,066 A | 10/1998 | Huitema et al. | |
| 5,827,177 A | 10/1998 | Oneda et al. | |
| 5,851,208 A | 12/1998 | Trott | |
| 5,855,569 A | 1/1999 | Komi | |
| 5,873,817 A | 2/1999 | Kokish et al. | |
| 5,899,425 A | 5/1999 | Corey, Jr. et al. | |
| 5,899,914 A | 5/1999 | Zirps et al. | |
| 5,904,647 A | 5/1999 | Ouchi | |
| 5,916,146 A | 6/1999 | Allotta et al. | |
| 5,916,147 A | 6/1999 | Boury | |
| 5,921,956 A | 7/1999 | Grinberg et al. | |
| 5,928,263 A | 7/1999 | Hoogeboom | |
| 5,938,678 A | 8/1999 | Zirps et al. | |
| 5,944,713 A | 8/1999 | Schuman | |
| 6,126,633 A | 10/2000 | Kaji et al. | |
| 6,174,280 B1 | 1/2001 | Oneda et al. | |
| 6,210,377 B1 | 4/2001 | Ouchi | |
| 6,210,378 B1 | 4/2001 | Ouchi | |
| 6,270,453 B1 | 8/2001 | Sakai | |
| 6,551,238 B2 | 4/2003 | Staud | |
| 6,623,424 B2 | 9/2003 | Hayakawa et al. | |
| 6,638,214 B2 | 10/2003 | Akiba | |
| 6,656,195 B2 | 12/2003 | Peters et al. | |
| 6,666,854 B1 * | 12/2003 | Lange | 606/1 |
| 6,752,756 B2 | 6/2004 | Lunsford et al. | |
| 6,761,717 B2 | 7/2004 | Bales et al. | |
| 7,090,637 B2 | 8/2006 | Danitz | |
| 7,147,650 B2 | 12/2006 | Lee | |
| 2002/0045803 A1 | 4/2002 | Abe et al. | |
| 2002/0095175 A1 | 7/2002 | Brock et al. | |
| 2002/0133173 A1 | 9/2002 | Brock et al. | |
| 2002/0156497 A1 | 10/2002 | Nagase et al. | |
| 2002/0177750 A1 | 11/2002 | Pilvisto | |
| 2002/0177847 A1 | 11/2002 | Long | |
| 2003/0065359 A1 | 4/2003 | Weller et al. | |
| 2003/0109898 A1 | 6/2003 | Schwarz et al. | |
| 2003/0135204 A1 | 7/2003 | Lee et al. | |
| 2003/0149338 A1 | 8/2003 | Francois et al. | |
| 2003/0216618 A1 | 11/2003 | Arai | |
| 2004/0049205 A1 | 3/2004 | Lee et al. | |
| 2004/0111009 A1 | 6/2004 | Adams et al. | |
| 2004/0138529 A1 | 7/2004 | Wiltshire et al. | |
| 2004/0176751 A1 | 9/2004 | Weitzner et al. | |
| 2004/0193146 A1 | 9/2004 | Lee et al. | |
| 2004/0236316 A1 | 11/2004 | Danitz et al. | |
| 2005/0049580 A1 | 3/2005 | Brock et al. | |
| 2005/0096694 A1 * | 5/2005 | Lee | 606/205 |
| 2005/0107667 A1 | 5/2005 | Danitz et al. | |
| 2005/0228440 A1 | 10/2005 | Brock et al. | |
| 2005/0251112 A1 | 11/2005 | Danitz et al. | |
| 2005/0273084 A1 | 12/2005 | Hinman et al. | |
| 2005/0273085 A1 | 12/2005 | Hinman et al. | |
| 2006/0195097 A1 | 8/2006 | Evans et al. | |
| 2006/0206101 A1 | 9/2006 | Lee | |
| 2006/0270909 A1 | 11/2006 | Davis et al. | |
| 2007/0250110 A1 * | 10/2007 | Lu et al. | 606/205 |

FOREIGN PATENT DOCUMENTS

| | | |
|---|---|---|
| EP | 0 448 284 A2 | 9/1991 |
| EP | 0 626 604 A2 | 5/1994 |
| EP | 0 427 949 B1 | 6/1994 |
| GB | 2 143 920 | 2/1985 |
| WO | WO 90/05491 | 5/1990 |
| WO | WO 92/01414 | 2/1992 |
| WO | WO 94/17965 | 8/1994 |

OTHER PUBLICATIONS

Ryoichi Nakamura et al., Multi-DOF Manipulator System for Laparoscopic Surgery, 8 pgs, Oct. 2004.

Ryoichi Nakamura et al., Development of Forceps Manipulator System for Laparoscopic Surgery, 6 pgs, Oct. 2001.

Hiromasa Yamashita et al., "Multi-Slider Linkage Mechanism for Endoscopic Forceps Manipulator," In Proc. of the 2003 IEEE/RSJ, Intl. Conference on Intelligent Robots and Systems, vol. 3, pp. 2577-2582, Las Vegas, Nevada, Oct. 2003.

* cited by examiner

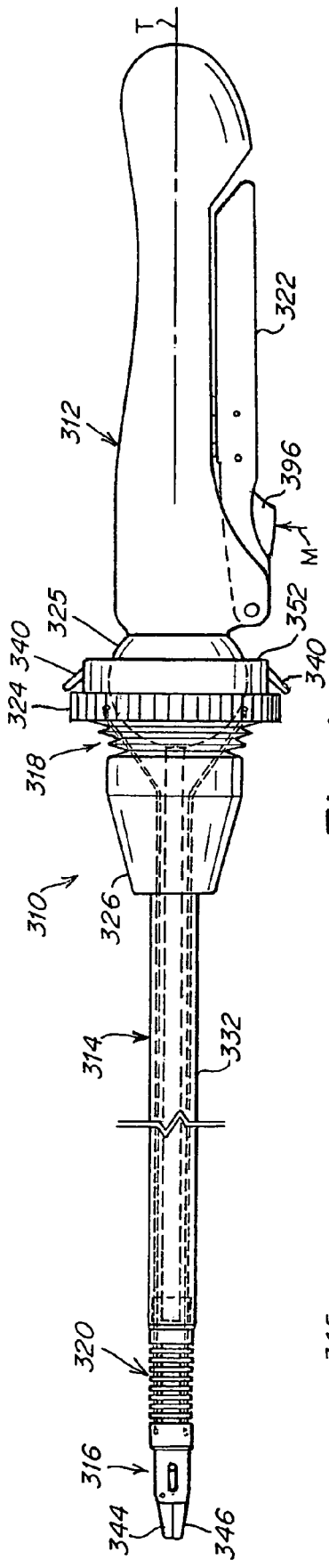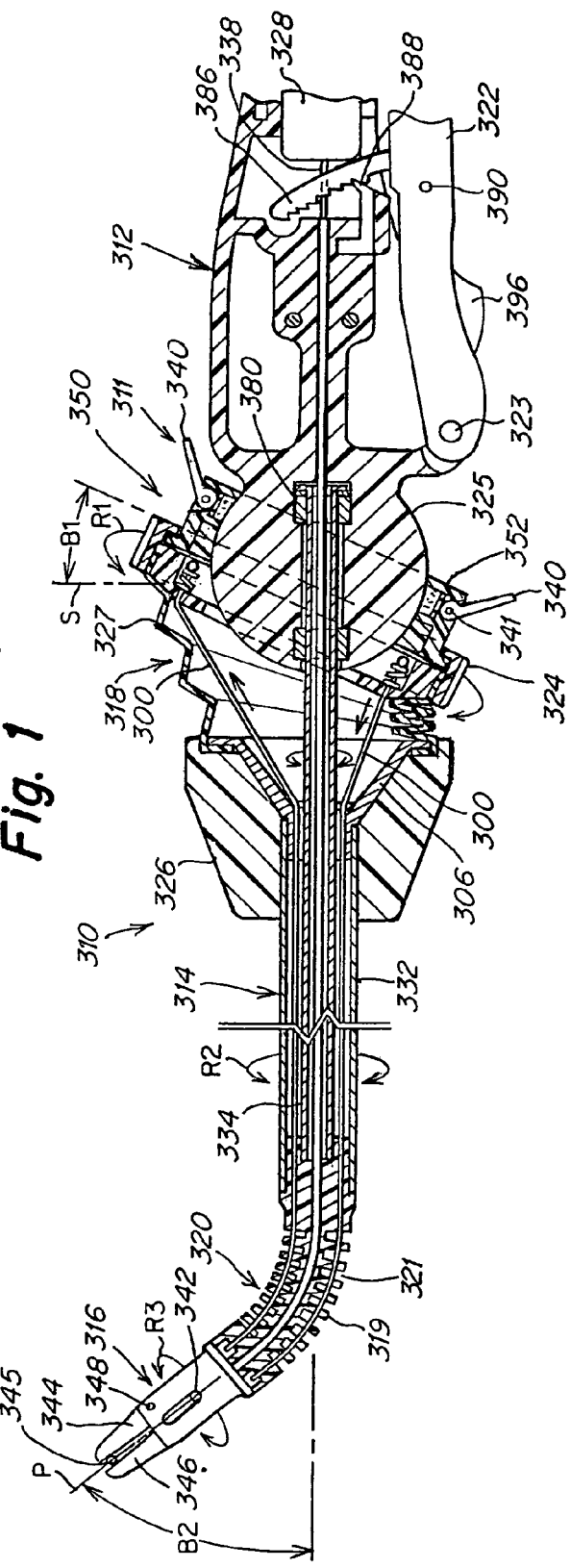

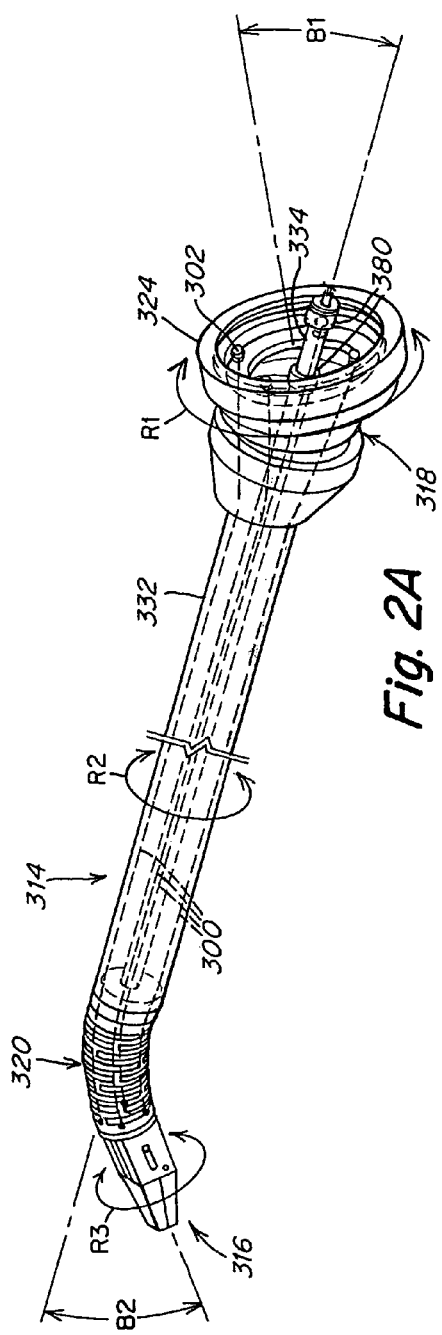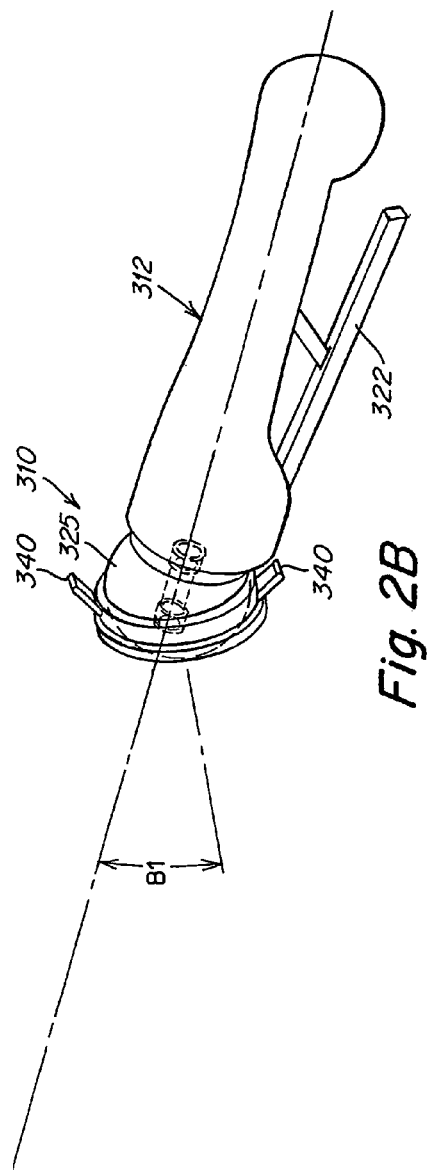
Fig. 2A
Fig. 2B

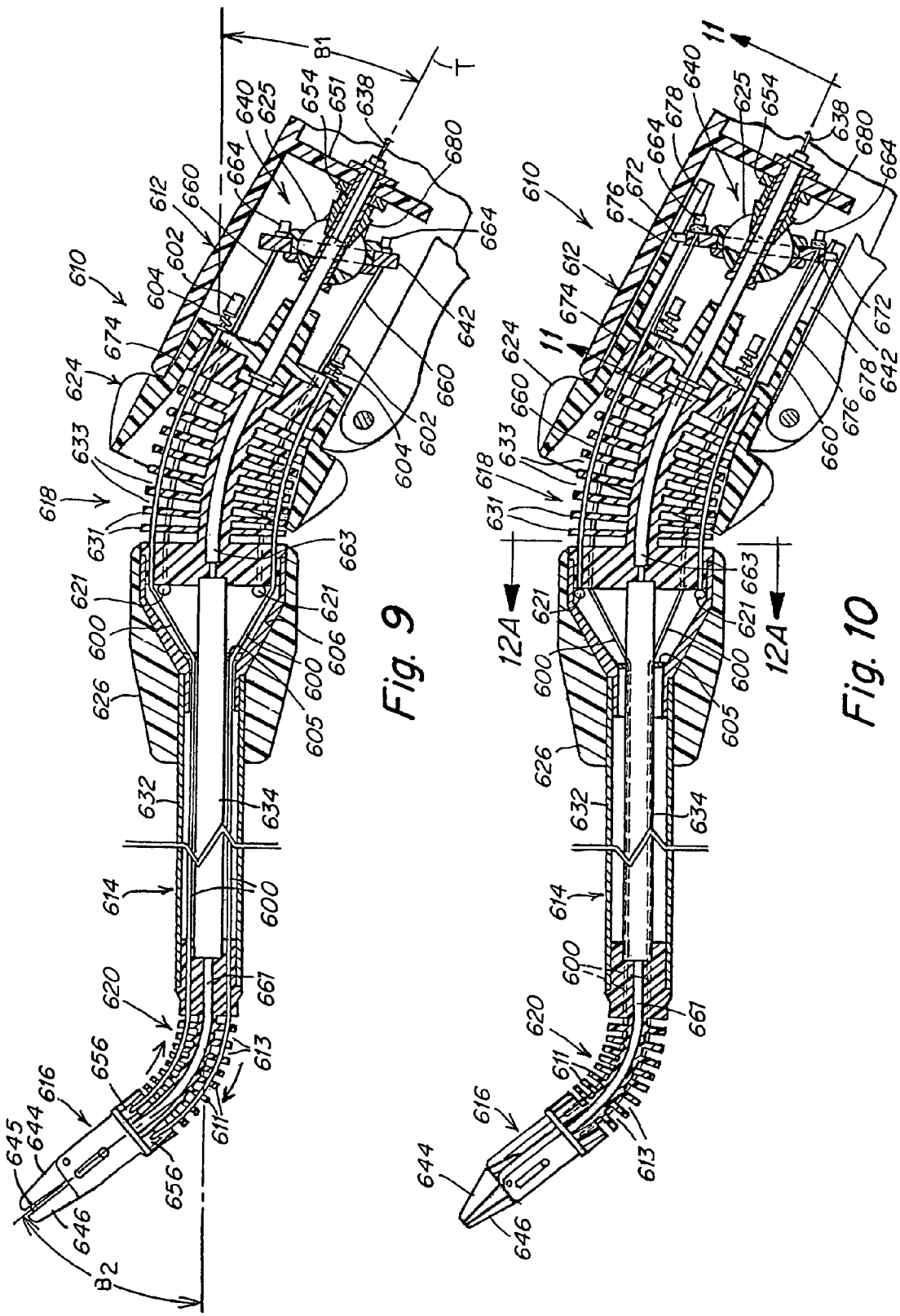

SURGICAL INSTRUMENT

RELATED APPLICATION

The present application claims priority to U.S. Provisional Application Ser. No. 60/811,046 filed on Jun. 5, 2006. The content of all of the aforementioned application is hereby incorporated by reference herein in its entirety.

TECHNICAL FIELD

The present invention relates in general to surgical instruments, and more particularly to manually-operated surgical instruments that are intended for use in minimally invasive surgery or other forms of surgical or medical procedures or techniques. The instrument described herein is primarily for laparoscopic or endoscopic procedures, however, it is to be understood that the instrument of the present invention can be used for a wide variety of other procedures, including intraluminal procedures.

BACKGROUND OF THE INVENTION

Endoscopic and laparoscopic instruments currently available in the market are extremely difficult to learn to operate and use, mainly due to a lack of dexterity in their use. For instance, when using a typical laparoscopic instrument during surgery, the orientation of the tool of the instrument is solely dictated by the locations of the target and the incision. These instruments generally function with a fulcrum effect using the patients own incision area as the fulcrum. As a result, common tasks such as suturing, knotting and fine dissection have become challenging to master. Various laparoscopic instruments have been developed over the years to overcome this deficiency, usually by providing an extra articulation often controlled by a separately disposed control member for added control. However, even so these instruments still do not provide enough dexterity to allow the surgeon to perform common tasks such as suturing, particularly at any arbitrarily selected orientation. Also, existing instruments of this type do not provide an effective way to hold the instrument in a particular position.

Accordingly, an object of the present invention is to provide an improved laparoscopic or endoscopic surgical instrument that allows the surgeon to manipulate the tool end of the surgical instrument with greater dexterity.

Another object of the present invention is to provide an improved surgical instrument that has a wide variety of applications, through incisions, through natural body orifices or intraluminally.

A further object of the present invention is to provide an improved medical instrument that is characterized by the ability to lock the instrument in a pre-selected particular position.

Another object of the present invention is to provide a locking feature that is an important adjunct to the other controls of the instrument enabling the surgeon to lock the instrument once in the desired position. This makes it easier for the surgeon to thereafter perform surgical procedures without having to, at the same time, hold the instrument in a particular bent configuration.

Still another object of the present invention is to provide an improved medical instrument that is characterized by the ability to lock the position of the instrument in a pre-selected position while enabling rotation of the tip of the instrument while locked.

SUMMARY OF THE INVENTION

To accomplish the foregoing and other objects, features and advantages of the present invention there is provided a medical instrument that comprising a proximal control handle; a distal work member; a proximal movable member controlled from the proximal control handle; a distal movable member controlled from the proximal movable member to provide controlled movement of the distal work member from the proximal control handle; an instrument shaft that intercouples the proximal and distal movable members; and actuation means coupled between said movable members. The proximal movable member comprises a movable ring assembly supported from the handle and adapted for three dimensional motion relative to the handle.

In accordance with other aspects of the present invention the medical instrument further including a locking member supported from the proximal control handle and having locked and unlocked states; the locking member in the unlocked state enabling control of the distal work member from the proximal control handle via the movable members; the locking member, in the locked state, holding the movable members in a desired fixed position; the locking member, in the locked state, fixes the position of the proximal movable member; the distal movable members comprise a uni-body structure; the movable ring assembly includes a rotation control member adjacent the proximal control handle for controlling the distal work member to rotate about a distal work member axis; the handle includes a ball end upon which the ring assembly is mounted for pivoting thereon in three dimensions; the ring assembly further includes a rider on the ball and at least one locking lever supported by said rider; the actuation means comprises a set of cables that couple between the turnable members and further including a cable retainer supported by the rotation control member and for retaining proximal ends of the cables; the proximal movable member comprises a bendable member that includes a bellows connected to the rotation control member, a rider and bearing means between the rotation control member and the rider; a ball is secured to the proximal end of the instrument shaft and received in a socket of the control handle; the ring assembly includes a rotation knob mounted for rotation relative to the handle; the actuation means comprises a set of cables that couple between the movable members and further including a cable retainer supported by the rotation control member and for retaining proximal ends of the cables; at least one locking lever supported by the handle and including a locking pad that is urged against the ball; the ring assembly includes a rotation control member and rider for controlling the distal work member to rotate about a distal axis, the handle including a ball end upon which the ring assembly is mounted for pivoting thereon, the ball end being split to receive a locking wedge to lock the position of the rider on the ball; a slide button for controlling the locking wedge position relative to the ball; the actuation means comprises cables and the rotation control member also includes a cable retainer for the proximal ends of the cables; and the proximal movable member comprises a bendable member that includes a bellows.

In accordance with another embodiment of the present invention there is provided a medical instrument having a proximal control handle and a distal tool that are intercoupled by an elongated instrument shaft that is meant to pass internally of an anatomic body, proximal and distal movable members that respectively intercouple the proximal control handle and the distal tool with the instrument shaft, cable actuation means disposed between the movable members and a locking means that is manually operable by a user and that includes a follower the position of which is responsive to the position of the movable members.

In accordance with other aspects of the present invention the movable members comprise bendable members, the cable actuation means comprising a first cable set disposed between the bendable members and further including a second cable set coupled between the follower and proximal bendable member; the cables of the second set terminate at the distal end of the proximal bendable member; both of the bendable members comprise uni-body members that include discs that define slots therebetween, the first cable set extending through both distal and proximal uni-body members while the second cable set extends through only the proximal uni-body member; the follower includes a ball and a rider supported on the ball, the second cable set connected to the rider to pivot the rider on the ball in response to bending at the proximal bendable member; a rotation member adjacent the proximal control handle is controllable to rotate the tool about its distal tool axis; the rotation member includes a pair of legs that define at least one slot for guiding at least one pin of the rider; the rotation member includes opposed legs that define opposed slots for receiving opposed pins of the rider; the ball is a split ball and the locking means further includes a wedge member that is operable in the locked state to engage the split ball to, in turn, freeze the position of the follower on the ball; the locking means comprises a slide button mounted at the handle and a wedge member responsive to the slide button for locking the position of the follower; the follower includes a ball and a rider supported on the ball, the ball being split for receiving the wedge member; and the slide button includes opposed ends that are respectively disposed on opposite sides of the handle and are manually actuable to either lock or unlock the instrument by depression thereof.

In accordance with another embodiment of the present invention there is provided a surgical instrument having a proximal control handle and a distal tool that are intercoupled by an elongated instrument shaft that is meant to pass internally of an anatomic body, proximal and distal movable members that respectively intercouple the proximal control handle and the distal tool with the instrument shaft, a first cable set disposed between the movable members to transfer control between the movable members, a follower disposed at the proximal control handle and a second cable set disposed between the follower and one of the movable members, the position of the follower being responsive to the position of the movable members.

In accordance with other aspects of the present invention the movable members comprise bendable members and further including a locking member that is manually operable by a user and that is adapted to fix the position of the follower when locked; the second cable set connects between the follower and the proximal bendable member; and the follower includes a ball and a rider supported on the ball, the second cable set connected to the rider to pivot the rider on the ball in response to bending at the proximal bendable member.

BRIEF DESCRIPTION OF THE DRAWINGS

It should be understood that the drawings are provided for the purpose of illustration only and are not intended to define the limits of the disclosure. The foregoing and other objects and advantages of the embodiments described herein will become apparent with reference to the following detailed description when taken in conjunction with the accompanying drawings in which:

FIG. 1 is a side elevation view of an embodiment of the surgical instrument of the present invention;

FIG. 2 is an enlarged fragmentary cross-sectional side view of the instrument shown in FIG. 1 with the instrument shown locked in a bent or angular position;

FIGS. 2A and 2B are schematic perspective views of the surgical instrument depicted in FIGS. 1 and 2 illustrating the instrument in separate sections including the handle as separate from the rest of the instrument;

FIG. 9 is a schematic cross-sectional side view of a further embodiment of the instrument using a different locking mechanism and shown with the instrument in a bent configuration;

FIG. 10 is a schematic cross-sectional side view of the instrument of FIG. 9 but with the rotation knob rotated through 45 degrees;

DETAILED DESCRIPTION OF THE PREFERRED EMBODIMENT

Figure 3:
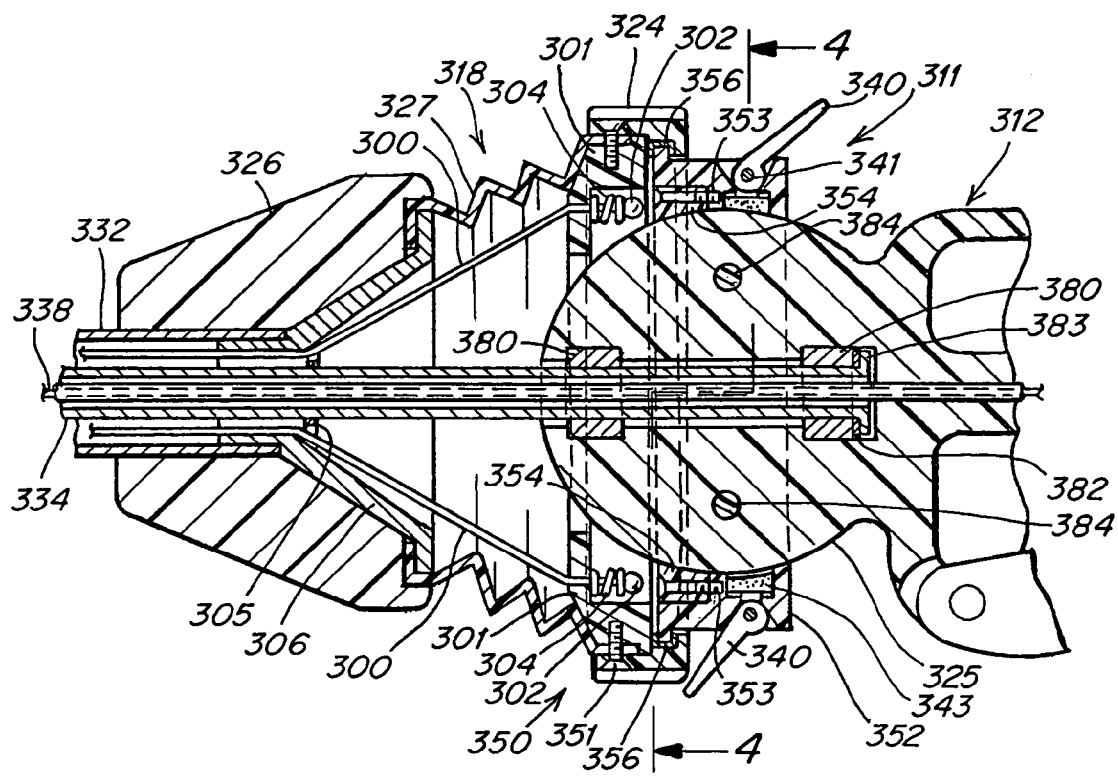
FIG. 3 is an enlarged fragmentary cross-sectional side view of the surgical instrument of FIGS. 19 and 20 and taken at the proximal bendable member.

The instrument of the present invention may be used to perform minimally invasive procedures. "Minimally invasive procedure," refers herein to a surgical procedure in which a surgeon operates through small cut or incision, the small incision being used to access the operative site. In one embodiment, the incision length ranges from 1 mm to 20 mm in diameter, preferably from 5 mm to 10 mm in diameter. This procedure contrasts those procedures requiring a large cut to access the operative site. Thus, the flexible instrument is preferably used for insertion through such small incisions and/or through a natural body lumen or cavity, so as to locate the instrument at an internal target site for a particular surgical or medical procedure. The introduction of the surgical instrument into the anatomy may also be by percutaneous or surgical access to a lumen or vessel, or by introduction through a natural orifice in the anatomy.

In addition to use in a laparoscopic procedure, the instrument of the present invention may be used in a variety of other medical or surgical procedures including, but not limited to, colonoscopic, upper GI, arthroscopic, sinus, thoracic, transvaginal and cardiac procedures. Depending upon the particular procedure, the instrument shaft may be rigid, semi-rigid or flexible.

Although reference is made herein to a "surgical instrument," it is contemplated that the principles of this invention also apply to other medical instruments, not necessarily for surgery, and including, but not limited to, such other implements as catheters, as well as diagnostic and therapeutic instruments and implements.

There are several different embodiments that are described herein. Basically, in all these embodiments preferably both the tool and handle motion members or bendable members are capable of bending in any direction. They are interconnected via cables in such a way that a bending action at the proximal member provides a related bending at the distal member. The proximal bending is controlled by a motion or deflection of the control handle by a user of the instrument. In other words the surgeon grasps the handle and once the instrument is in position any motion at the handle (deflection) immediately controls the proximal bendable member which, in turn, via cabling controls a corresponding bending or deflection at the distal bendable member.

The proximal member is preferably generally larger than the distal member so as to provide enhanced ergonomic control. In one version in accordance with the invention there may be provided a bending action in which the distal bendable member bends in the same direction as the proximal bendable member. In an alternate embodiment the bendable, turnable or flexible members may be arranged to bend in opposite directions by rotating the actuation cables through 180 degrees, or could be controlled to bend in virtually any other direction depending upon the relationship between the distal and proximal support points for the cables.

It should be noted that the amount of bending motion produced at the distal bending member is determined by the dimension of the proximal bendable member in comparison to that of the distal bendable member. In the embodiment described the proximal bendable member is generally larger than the distal bendable member, and as a result, the magnitude of the motion produced at the distal bendable member is greater than the magnitude of the motion at the proximal bendable member. The proximal bendable member can be bent in any direction (about 360 degrees) controlling the distal bendable member to bend in either the same or an opposite direction, but in the same plane at the same time. Also, as depicted in FIG. 2, the surgeon is able to bend and roll the instrument's tool about its longitudinal axis at any orientation simply by rolling the axial rotation knob.

In this description reference is made to bendable members. These members may also be referred to as turnable members or flexible members. In the descriptions set out herein, terms such as "bendable section," "bendable segment," "bendable motion member," or "turnable member" refer to an element of the instrument that is controllably bendable in comparison to an element that is pivoted at a joint. The term "movable member" is considered as generic to bendable sections and joints. The bendable elements of the present invention enable the fabrication of an instrument that can bend in any direction without any singularity and that is further characterized by a ready capability to bend in any direction. One form of bendable members shown herein includes a single unitary or uni-body structure. Another form of bendable member disclosed herein is a ball and rider structure. A definition of these bendable motion members is—an instrument element, formed either as a controlling means or a controlled means, and that is capable of being constrained by tension or compression forces to deviate from a straight line to a curved configuration without any sharp breaks or angularity—. Bendable members may be in the form of unitary structures, such as shown herein in FIG. 9, may be constructed of engageable discs, or the like, or may include bellows arrangements. A definition of a "unitary' or "uni-body" structure is,—a structure that is constructed only of a single integral member and not one that is formed of multiple assembled or mated components.

A first embodiment of the invention is described herein in FIGS. 1-4 and includes the functions of bending, rotation and locking all as to be described in more detail hereinafter. The surgical instrument 310 is comprised of a handle 312 at the proximal end of the instrument, an elongated instrument shaft 314 and a tool or end effector 316 disposed at the distal end of the surgical instrument. The tool may take on a number of different configurations including, but not limited to, articulating and non-articulating tools. In the disclosed embodiment the instrument shaft 314 is rigid, usually of a metal material, although it may also be constructed so as to be at least partially inherently flexible or bendable. For normal laparoscopic procedures the instrument shaft 314 is usually rigid. For an example of a flexible instrument shaft used intraluminally refer herein to FIGS. 14 and 15 of related U.S. application Ser. No. 10/822,081, filed on Apr. 12, 2004 which is hereby incorporated by reference herein in its entirety. Also incorporated by reference in their entirety are U.S. application Ser. No. 11/185,911 filed on Jul. 20, 2005; U.S. application Ser. No. 11/242,642 filed on Oct. 3, 2005 and U.S. application Ser. No. 11/302,654 filed on Dec. 14, 2005.

The handle 312 may be comprised of two handle halves. A lever 322 is manipulatable by the surgeon as the handle is grasped for opening and closing the end effector 316 at the distal end of the instrument shaft 314. In FIG. 2 the end effector is illustrated as comprised of a movable jaw 344 and a fixed jaw 346. The rotation knob 324 at the proximal end of the instrument is used to rotate the instrument shaft and end effector. This rotation is illustrated in FIG. 2 by the circular arrow R1. In FIG. 2 a coordinate system expressed by the X-Y-Z axes may be considered with axis Z being the axis of the instrument shaft. The roll of the instrument indicated by the arrows R1, R2 and R3 is in relationship to the Z axis.

FIGS. 2 and 3 also illustrate an adaptor cover 326 for partially retaining a portion of the proximal bendable member 318. At the distal end of the instrument shaft 314, there is provided the distal motion or bendable member 320. The member 320 may be at least partially covered by a sheath-like cover (not shown) that may be a thin plastic or rubber flexible tube that readily deflects as the distal bendable member is actuated from the proximal bendable member via the handle. For instruments such as a needle holder or a suture assist device, the compliant cover is beneficial in preventing the suture from catching while tying a knot. However, for other applications one may choose not to use the cover so as to simplify the instrument and its fabrication. Other components, such as the knob 324, adaptor cover 326 and bendable members are preferably formed of a plastic material.

The instrument of the present invention is preferably constructed to be disposable or alternatively resposable. Accordingly, to make the instrument as inexpensively as possible as many of the components as possible are made of a plastic material.

The surgical instruments that are described herein may be used for laparoscopic surgery through the abdominal wall. For this purpose there is provided an insertion site at which there is disposed a cannula or trocar (not shown). The shaft 314 of the instrument is adapted to pass through the cannula so as to dispose the distal end of the instrument at an operative site. The end effector 316 is disposed at such an operative site. A rolling motion can be carried out with the instrument of the present invention. This can occur by virtue of the rotation of the rotation knob 324 relative to the handle 312 about the handle axis T which is essentially the longitudinal center line of the handle. This is illustrated in FIG. 2 by the circular arrow R1. When the rotation knob 324 is rotated, in either direction, this causes a corresponding rotation of the instrument shaft 314 about the aforementioned Z axis. This is depicted in FIG. 2 by the rotational arrow R2. This same motion also causes a rotation of the end effector 316 about axis P as illustrated by the rotational arrow R3 in FIG. 2. Refer also to FIG. 2A for a showing of the rotational arrows. In FIG. 2 the rotation knob 324 is shown tilted relative to transverse axis S at an angle B1. In the position of FIG. 2 the rotation knob can be rotated relative to the rider 352. By means of the cabling 300 a bending at the proximal bendable member 318 causes a corresponding bend at the distal bendable member 320 to a position wherein the tip is directed along axis P and at an angle B2 to the instrument shaft longitudinal center axis.

The combination of manipulation via the bendable members and rotation via the knob 324 provides a very precise and ergonomically comfortable degree of control for the surgeon. The instrument may be used in a number of different ways. In this particular embodiment, rather than tilting the handle itself, the handle is maintained in line with the instrument shaft, and the rotation knob (in combination with the locking mechanism 311) is manipulated to both rotate in the direction of arrow R1, as well as to tilt or rotate on the ball 325 in essentially any direction. As shown in FIGS. 2 and 3, the ball 325 is an integral part of the handle 312. Thus, the handle 312 may be grasped in the palm and the fingers and thumb may be used to manipulate the rotation knob 324 enabling tilting of the rotation knob in pitch and yaw, as well as rotation thereof, in controlling the end effector. One or more of the fingers may also be used to actuate the end effector from the lever 322.

In the drawings a set of jaws is depicted, however, other tools or devices may be readily adapted for use with the instrument of the present invention. These include, but are not limited to, cameras, detectors, optics, scope, fluid delivery devices, syringes, etc. The tool may include a variety of articulated tools such as: jaws, scissors, graspers, needle holders, micro dissectors, staple appliers, tackers, suction irrigation tools and clip appliers. In addition, the tool may include a non-articulated tool such as: a cutting blade, probe, irrigator, catheter or suction orifice.

In FIG. 2 the cabling within the instrument shaft is shown controlling the instrument in a bent condition with the end effector bent upwardly as shown. The end effector or tool 16 is actuated by means of a jaw actuation means which is comprised primarily of the elongated lever 322 at the proximal end of the instrument. The lever 322 is supported from the housing at the lever pivot pin 323. The closing of the lever 322 against the handle 312 acts upon a slider 328 which is used to capture the very proximal end of the actuation cable 338. When the lever 322 is un-actuated (separated from the handle housing) this corresponds to the end effector jaws being in a fully open position. When the lever 322 closes this causes the slider to move toward the right as depicted in FIG. 2, and then the jaws 344 and 346 are moved toward a closed position. In FIG. 2 the jaws are illustrated as closed so as to grasp, for example, a needle 345.

The instrument shaft 314 includes an outer shaft tube 332 that may be constructed of a light weight metal material or may be a plastic material. Alternatively, the tube 332 may be flexible for intraluminal use. The proximal end of the tube 332 is received by the adaptor cover 326. The distal end of the tube 332 is secured to the distal bendable member 320. Refer to FIG. 2 for some further details of the distal bendable member 320. Within the outer shaft tube 332 there is provided a support tube 334 that is preferably constructed of a metal material, but could also be made of a rigid plastic material. Tube 334 extends between the distal bendable or flexible member 320 and the proximal bendable or flexible member 318, and further extends into the ball 325 of the handle. The jaw actuator cable 338 extends within this support tube 334. The support tube 334 may support along its length a plurality of spacers, only one of which is shown in FIG. 3 at 305. Each of the spacers may be evenly spaced and provided with diametric guide slots for the cables.

As indicted previously, the end effector 316 is comprised of a pair of jaws 344 and 346. These jaws may be used to grasp a needle 345 or other item. The upper jaw 344 fits within a channel (not shown) in the lower jaw 346. A pivot pin 348 is used between the jaws to enable rotation therebetween. A translation pin 342 extends through slots of the jaws and engages with the jaw actuator cable 338. When the lever 322 is in its rest position the jaws are fully open. In that position the pin 342 is at a more distal location maintaining the jaw in an open position. As the cable 338 is pulled, then the pin 342 moves to the right in the slots, causing the jaws 344 and 346 to pivot toward a closed position as depicted in FIG. 2.

The jaw actuator cable 338 terminates at its respective ends at the end effector and at a rotation barrel (not shown) supported in the slider 328 (see FIG. 2). Within the distal bendable sections 320 there may be provided a plastic tube. This tube may be constructed of a plastic such as polyethyletherkeytone (PEEK). The material of the tube is sufficiently rigid to retain the cable 338 and yet is flexible enough so that it can readily bend with the bending of the bendable member 320. The tubes have a sufficient strength to receive and guide the cable, yet are flexible enough so that they will not kink or distort, and thus keep the cable in a proper state for activation, and also defines a fixed length for the cable. The tube is longitudinally stiff, but laterally flexible.

The control of the end effector 316 is by means of the jaw actuator cable 338. As mentioned previously the very proximal end of the jaw actuator cable 338 is retained at the slider 328. A link (not shown) connected from the lever 322 is the main means for actuating the slider 328 and, in turn, the actuator cable 338 from the lever 322. Refer to related provisional application Ser. No. 60/802,885 filed on May 23, 2006 for further details of the tool actuation means particularly the part within the handle 312 and which is hereby incorporated by reference in its entirety.

The lever 322 actuates the end effector as it is pressed toward the handle body. The lever 322 operates with a ratchet and pawl arrangement with the lever capable of being depressed in ratcheted increments. This ratchet and pawl arrangement includes the ratchet 386 and pawl 388. To accommodate the ratchet 386, the slider 328 is provided with an end dish out or cut out. The pawl 388 is retained by the handle. The ratchet 388 pivots at the pivot pin 390 and is provided with a series of ratchet teeth that can hold the ratchet in successive positions corresponding to successive degrees of closure of the end effector. A torsion spring (not shown) is disposed partially about the pivot 390 and urges the ratchet teeth into contact with the pawl 388.

The ratchet and pawl arrangement also includes an integral release means that is usually engageable by the surgeon's thumb. As depicted in FIG. 2, on one side of the pivot 390 there is the pawl 386 and on the other side of the pivot there is an arm that supports a release button 396. When a force is directed against the button 396 in the direction of arrow M in FIG. 1 then this releases the ratchet and pawl arrangement and returns the lever 322 to its released position with the jaws fully opened. The pressing of the button 396 rotates the ratchet out of engagement with the pawl.

Reference is now made to the cabling that extends between the proximal and distal bendable members. This cabling is provided so that any bending at the proximal bendable member is converted into a corresponding bending at the distal bendable member. The bendable members that are described herein enable bending in all directions. In the preferred embodiment described herein, the distal bendable member is smaller than the proximal bendable member. However, as indicated before other size relationships can be used depending upon the particular use of the instrument and the medical procedure in which it is being used.

The control between the proximal bendable or turnable member 318 and the distal flexible, bendable or turnable member 320 is carried out by means of the flex control cables 300. There are four such cables in the illustrated embodiment identified, for example, in FIG. 2A. At the proximal end of these cables, the cables connect to the anchors or cable end lugs 302. Four springs 304 are retained between these end lugs 302 and the annular cable retainer 301. Refer to FIG. 3 for an illustration of the end lugs 302 and the springs 304. The springs 304 tension or take up the slack on the cables. Between the bendable members, the cables 300 may be guided by means of the slots in spacers (only one shown) that may be disposed along the support tube 334. Within the adaptor cover 326, the cables 300 extend through the transition member 306. The cables then extend to a larger outer diameter locus as they extend through the proximal bendable member as depicted in FIGS. 2 and 3. The stepped transition member 306 may be of metal and is disposed adjacent to the proximal end of tube 334.

FIGS. 1 and 2 depict the distal end of the instrument and, in particular, the distal flexible member 320. This is in the form of a unitary member which may be the same as that described in U.S. Ser. No. 11/185,911, filed on Jul. 21, 2005, which is hereby incorporated by reference in its entirety. Briefly, this distal bendable member is comprised of a single piece slotted uni-body or unitary structure comprised of alternating slots and discs. The discs are supported from a central member. FIGS. 1 and 2 illustrate the discs 319 that define therebetween the annular slots 321. Between adjacent discs there may also be provided connecting ribs (not shown). Clearance holes are provided for receiving the cables 300. These clearance holes are provided in the ribs and discs. To align the distal flexible member with the shaft tube 332, there may be provided an alignment tab on the distal bendable member 320 and a corresponding slot in the tube 332.

The proximal motion member 318 is constructed primarily as a bellows 327 that functions with the rotation knob 324 and locking mechanism 311 to control the distal end of the instrument. The bellows 327 is attached at opposite ends to the adaptor 326 at member 306 and at the rotation knob 324. The ends of the bellows may be secured by a compression fit with the respective adaptor 326 and rotation knob 324. As illustrated in FIGS. 2 and 3 the bellows are constructed as an accordion pleat and have a relatively rigid construction so that they are relatively stiff in the rotational direction, and yet are readily flexible (foldable) in the longitudinal direction. Any rotation imparted to the rotation knob 324 is coupled via the bellows 327 to the adaptor 326 and instrument shaft 314, and from there to the distal end of the instrument to rotate the end effector. Thus, in this embodiment the handle is maintained at an in-line position relative to the instrument shaft while the rest of the instrument that is distal thereof can be rotated via the rotation knob. Further, bending is controlled via the rotation knob and rider in conjunction with the ball of the handle.

The embodiment described in FIGS. 1-4 also includes a lock feature that enables the position between the proximal and distal motion members to be fixed in a predetermined position, such as the position illustrated in FIG. 2 where the rotation knob and lock mechanism have been bent, pivoted or rotated causing a corresponding bending of the tool upwardly. Once the surgeon has the instrument in the desired bent position then the locking mechanism is used to conveniently hold the instrument in that position. The specific locking member is shown in FIGS. 2 and 3 as provided by the opposed lock levers 340 that are pivotally supported at pins 341. For the purpose of illustration, FIG. 3 shows the bottom lock lever 340 in its released position in which the bendable members are permitted to bend in the normal operation of the instrument without being locked, while the top lock lever 340 in FIG. 3 is shown in its locked position. The locking levers are each also provided with a friction pad 343 (FIG. 3) for engaging the ball 325.

In this embodiment, although a pair of lock levers is illustrated it is understood that only a single lock lever may be used. When a pair of lock levers is used they are normally both held in the same position, either locked or unlocked. This locking feature is an important adjunct to the other controls of the instrument enabling the surgeon to lock the instrument once in the desired position. This makes it easier for the surgeon to thereafter perform surgical procedures without having to, at the same time, hold the instrument in a particular bent configuration.

Thus, the control at the handle is used to bend the instrument at the proximal bendable member to, in turn, control the positioning of the distal bendable member and tool. The "position" of the tool is determined primarily by this bending action and may be considered as the coordinate location at the distal end of the distal bendable member. Actually, one may consider a coordinate axis at both the proximal and distal bendable members as well as at the instrument tip. This positioning is in three dimensions. The "orientation" of the tool, on the other hand, relates to the rotational positioning of the tool about the illustrated distal tip axis (see axis P in FIG. 3).

In the embodiment of FIGS. 1-4 the position of the end effector is set by means of an oscillating or movable ring assembly 350 that may be considered as including, inter alia, the aforementioned rotation knob 324, levers 340, annular cable retainer 301 and locking mechanism 311. This ring assembly 350 also includes the rider 352, retainer ring 354, bearing 356 and fasteners. The ring assembly 350 is manipulated via the rotation knob 324 to control the cabling to the end effector and in a pitch and yaw manner. This action pushes and pulls the cabling to set the position of the end effector. At the same time the rotation knob 324 may be rotated to rotate the tip of the instrument about its tip axis. See axis P and rotational arrow R3 in FIG. 2. In FIG. 2 the levers 340 are shown in their locked position to thus clamp the ring assembly 350 to the handle ball 325. Any rotation of the rotation knob 324 while the instrument is locked (or unlocked) maintains the instrument tip at the same angular position, but rotates the orientation of the tip (tool). For a further explanation of the rotational feature refer to co-pending application Ser. No. 11/302,654, filed on Dec. 14, 2005, particularly FIGS. 25-28, which is hereby incorporated by reference in its entirety.

Figure 4:
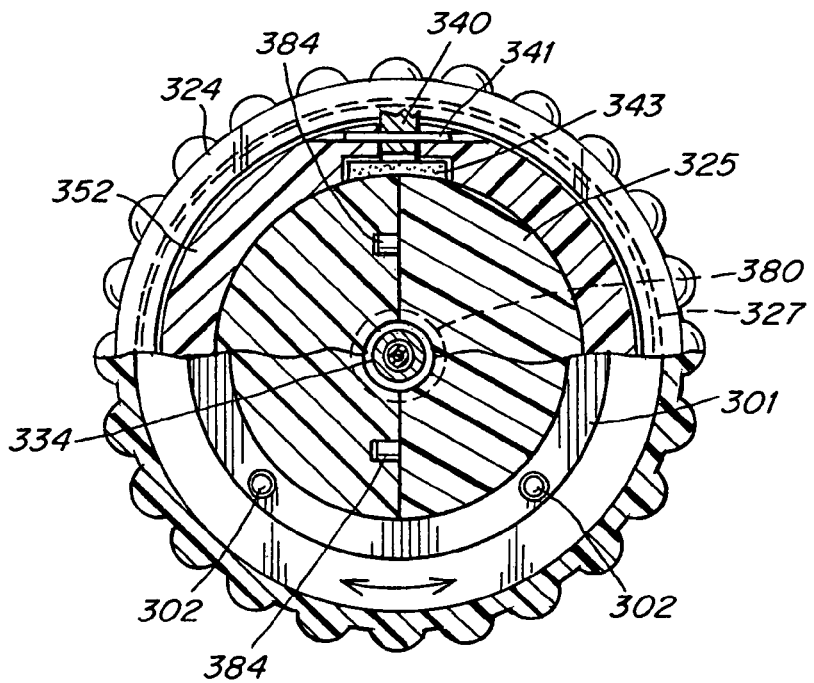
FIG. 4 is a cross-sectional side view of the instrument illustrated in FIGS. 1-3 and as taken along line 4-4 of FIG. 3.

Refer now to FIGS. 3 and 4 for further details of the movable or rotatable ring assembly 350. The annular cable retainer 301 and rotation knob 324 form a unit that is held together by a plurality of securing screws 351. This unit is rotational by means of the bearing 356 relative to the rider 352. The annular rider 352 is secured with the retaining ring 354 by means of a plurality of securing screws 353. Thus, any rotation of the rotation knob 324 causes a rotation of the cable retainer 301 and the associated cables 300. The rider 352 and retaining ring 354 capture the handle ball 325 and have their inner surfaces conform to the shape of the spherical ball 325. The rider 352 is supported so as to be free to pitch and yaw on the ball 325, while the rotation knob 324 is free to rotate relative to the rider 352. The user of the instrument can manipulate the rotation knob and rider separately with separate fingers. FIG. 2 shows the ring assembly 350 tilted to provide a like tilt of the end effector, while FIG. 3 shows the ring assembly 350 at a neutral position which corresponds to a straight position of the distal end of the instrument.

FIGS. 3 and 4 also show the bearings 380 that enable the inner shaft 334 to rotate relative to the fixed ball 325 when the instrument shaft is rotated from the rotation knob 324. The inner shaft 334 is illustrated as having a proximal end collar 383 for positioning and supporting the inner shaft relative to the bearings. A thrust washer 382 may also be provided between the bearing 380 and collar 383. The handle itself is preferably provided in two halves joined by locating pins 384 in the ball 325.

Figure 5:
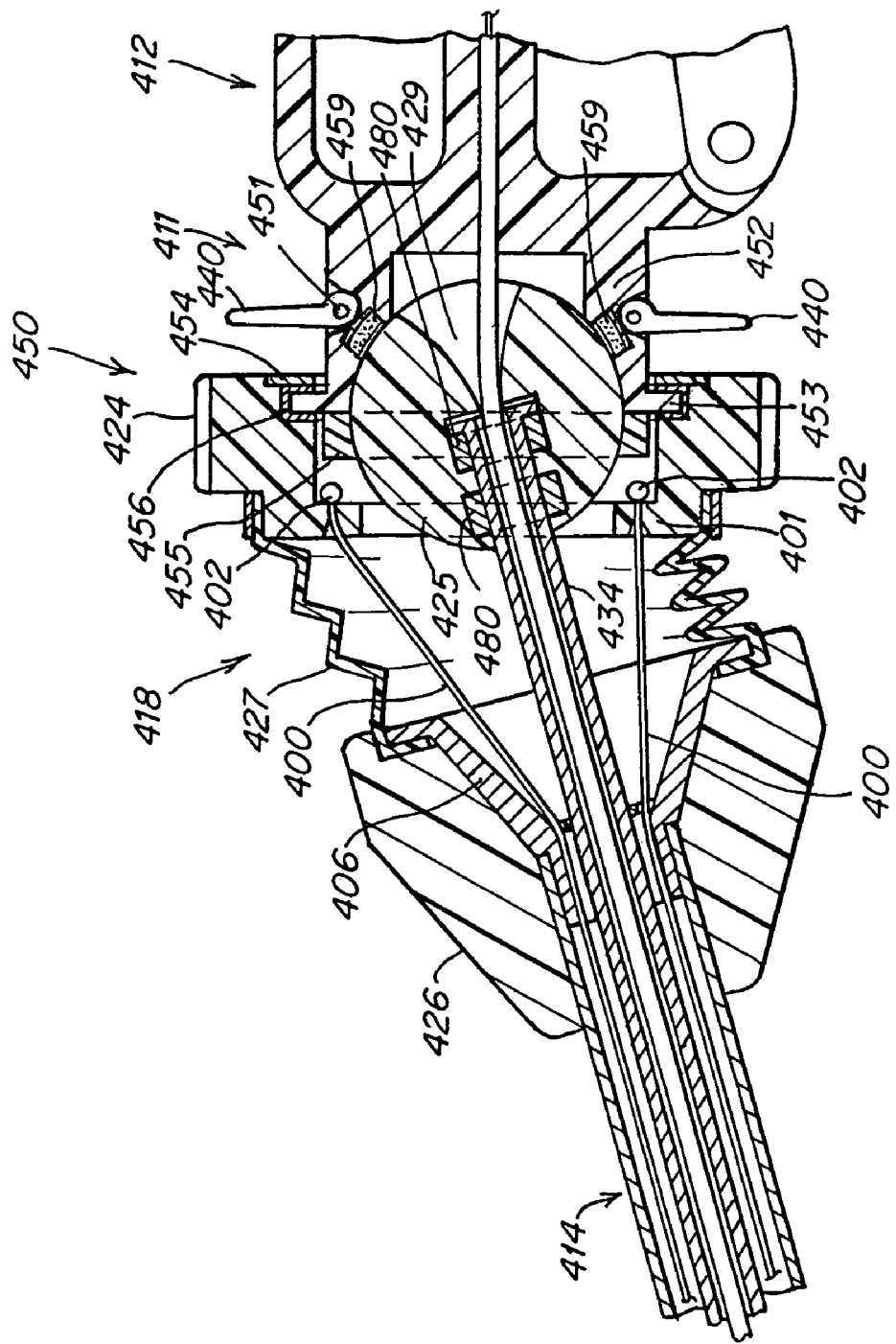
FIG. 5 is a somewhat enlarged fragmentary cross-sectional view of an alternate embodiment of the present invention similar to that shown in FIG. 2.
Figure 5A:
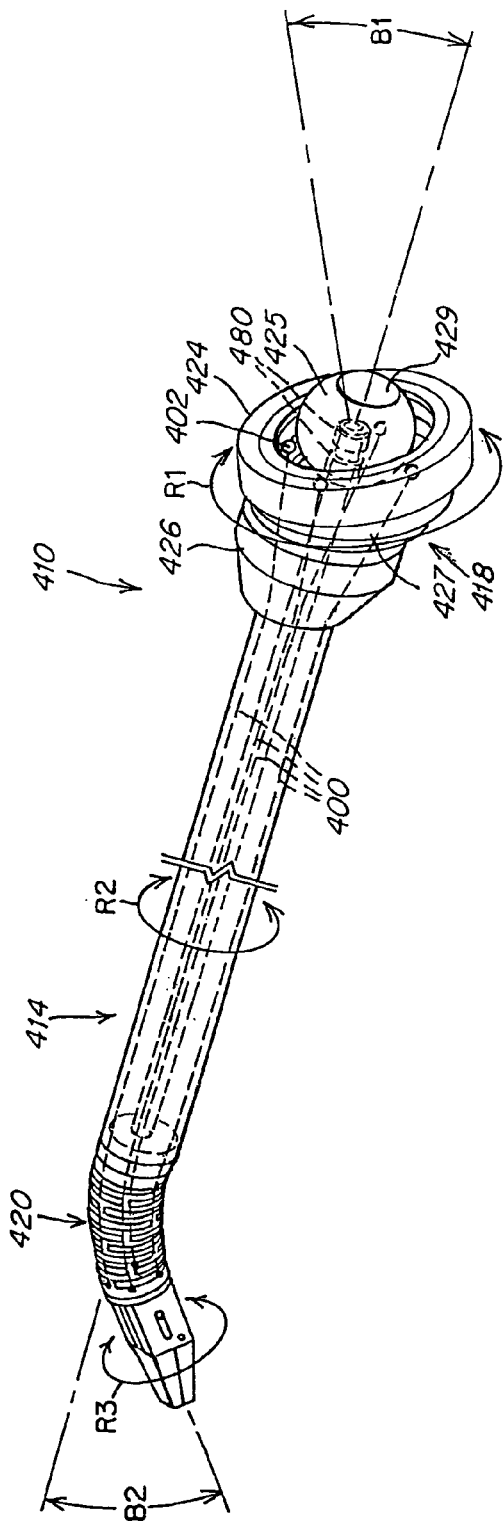
FIGS. 5A and 5B are schematic perspective views of the surgical instrument depicted in FIG. 5 illustrating the instrument in separate sections including the handle as separate from the rest of the instrument.
Figure 5B:
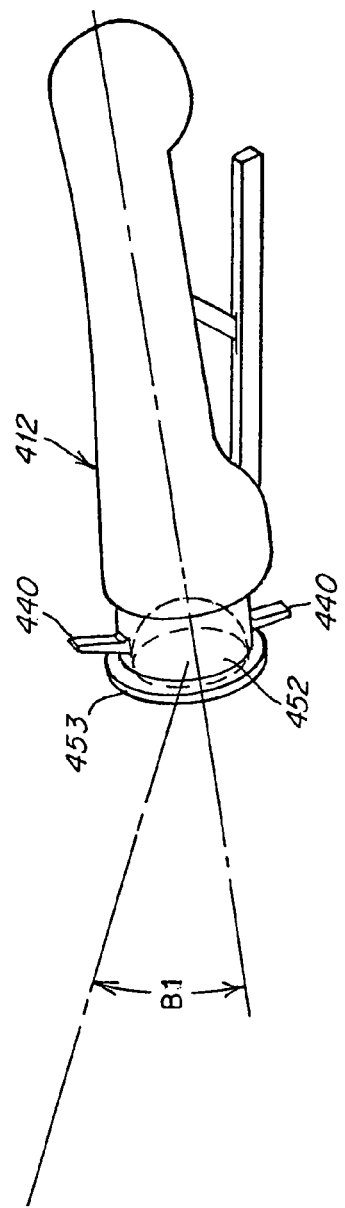

Reference is now made to FIGS. 5, 5A and 5B for a description of another embodiment of the present invention. The surgical instrument 410 is comprised of a handle 412 at the proximal end of the instrument, an elongated instrument shaft 414 and a tool or end effector 416 disposed at the distal end of the surgical instrument. The instrument shaft and distal end of the instrument in this embodiment may be substantially identical to the embodiment illustrated in FIGS. 1 and 2. The embodiment of FIG. 5 also illustrates an adaptor cover 426 for partially retaining a portion of the proximal bendable member 418. At the distal end of the instrument shaft 414, there is provided the distal motion or bendable member 420.

In the embodiment of FIG. 5 rather than the ball being attached to the handle, the ball 425 is attached to the proximal end of the instrument shaft and thus the handle 412 can bend or deflect at its rider 452. The axis of the handle shifts as the rider rotates on the ball 425. This action bends the proximal bendable member 418, such as to the position shown in FIG. 5. The positioning of the end effector is set or controlled by changing the angle of the handle relative to the instrument shaft. Once the tool is in the desired position then the locking mechanism 411 clamps the ball and socket (rider) together.

The proximal motion member 418 is constructed primarily of a bellows 427 that functions with the rotation knob 424 and locking mechanism 411 to control the distal end of the instrument. The bellows 427 is attached at opposite ends to the adaptor 426 at member 406 and at the rotation knob 424. The ends of the bellows may be secured by a compression fit with the respective adaptor 426 and rotation knob 424. As illustrated in FIG. 5 the bellows are constructed as an accordion pleat and have a relatively rigid construction so that they are relatively stiff in the rotational direction, and yet are readily flexible (foldable) in the longitudinal direction. Any rotation imparted to the rotation knob 424 is coupled via the bellows 427 to the adaptor 426 and instrument shaft 414, and from there to the distal end of the instrument to rotate the end effector. Thus, in this embodiment the handle is tilted on the ball to control the proximal bendable member which, in turn, controls the position of the distal bendable member. While in any bent position the rotation knob is used to rotate the tip of the instrument about the tip axis.

In the embodiment of FIG. 5 the position or location of the end effector is set by means of a ring assembly 450 that may be considered as including, inter alia, the aforementioned rotation knob 424, as well as the levers 440, annular cable retainer 401 and locking mechanism 411. This ring assembly 450 also includes the rider 452 with its flange 453, retaining rings 454 and 455, bearing 456 and fasteners. The ring assembly 450 is manipulated via the rotation knob 424 to control the cabling to the end effector and in a pitch and yaw manner. This action pushes and pulls the cabling to set the position of the end effector. At the same time the rotation knob 424 may be rotated to rotate the tip of the instrument about its tip axis. See axis P and rotational arrow R3 in FIG. 2. In FIG. 5 the levers 440 are shown in their unlocked position to thus unclamp the ring assembly 450 relative to the ball 425. Any rotation of the rotation knob 424 while the instrument is locked (or unlocked) maintains the instrument tip at the same angular position, but rotates the instrument orientation of the tip of the instrument at the end effector.

Refer now to FIG. 5 for further details of the ring assembly 450. The annular cable retainer 401 and rotation knob 424 form a unit that may be constructed of one or separate parts. This unit is rotational by means of the bearing or bushing 456 relative to the flange 453 of the rider 452. The annular rider 452 may be secured with the retaining ring 455 by means of one or more securing screws. Any rotation of the rotation knob 424 causes a rotation of the cable retainer 401 and the associated cables 400. FIG. 5 also shows the cables terminating at their proximal ends at the end lug 402. A spring or resilient member may be associated with each securing lug 402. The rider 452 and retaining ring 455 capture the shaft ball 425 and have their inner surfaces conform to the shape of the spherical ball 425. The rider 452 is supported so as to be free to pitch and yaw on the ball 425, while the rotation knob 424 is free to rotate relative to the rider 452. A second retainer 454 is fastened to the knob 424 about the flange 453. The user of the instrument can manipulate the rotation knob and rider separately with separate fingers. FIG. 5 shows the ring assembly 450 tilted to provide a like tilt of the end effector.

FIG. 5 also shows the bearings 480 that enable relative rotation between the inner shaft 434 and the ball 425 when the instrument shaft is rotated from the rotation knob 424. The inner shaft 434 may have a proximal end collar as shown in FIG. 3 for positioning and supporting the inner shaft relative to the bearings. A thrust washer may also be provided between the bearing 480 and collar. The handle may be provided in two halves joined by locating pins in the ball 425. FIG. 5 also shows an expanded or flared channel at 429 in the ball 425. This configuration assists in the free rotation of the handle to enable a bending of the actuator cable tube, such as in a position illustrated in FIG. 5.

The embodiment described in FIG. 5 also includes a lock feature that enables the relative position between the proximal and distal motion members to be fixed in a predetermined position, such as the position illustrated in FIG. 5 where the rotation knob and lock mechanism have been bent, pivoted or rotated causing a corresponding bending of the tool. Once the surgeon has the instrument in the desired bent position then the locking mechanism is used to conveniently hold the instrument in that position. However, even though locked, the tool orientation can be changed via the rotation knob, or the like. The specific locking member is shown in FIG. 5 as provided by the opposed lock levers 440 that are pivotally supported at pins 441. FIG. 5 shows the both lock levers 440 in their released position in which the bendable members are permitted to bend in the normal operation of the instrument without being locked. The levers 440 are pivoted toward the rider 452 to urge the lever pad 459 into engagement with the ball 425.

In this embodiment although a pair of lock levers is illustrated it is understood that only a single lock lever may be used. When a pair of lock levers is used they are normally both held in the same position, either locked or unlocked. This locking feature is an important adjunct to the other controls of the instrument enabling the surgeon to lock the instrument once in the desired position. This makes it easier for the surgeon to thereafter perform surgical procedures without having to, at the same time, hold the instrument in a particular bent configuration. However, even when locked, the end effector can still be rotated to control tool orientation.

Refer now also to FIGS. 5A and 5B. These are perspective views of respective parts of the instrument of FIG. 5. FIG. 5A shows the instrument part that includes everything from the rotation knob to the distal end of the instrument. This includes the proximal and distal bendable members, the instrument shaft and the end effector. FIG. 5B shows the handle part of the instrument along with the rider flange and locking levers.

Figure 6:
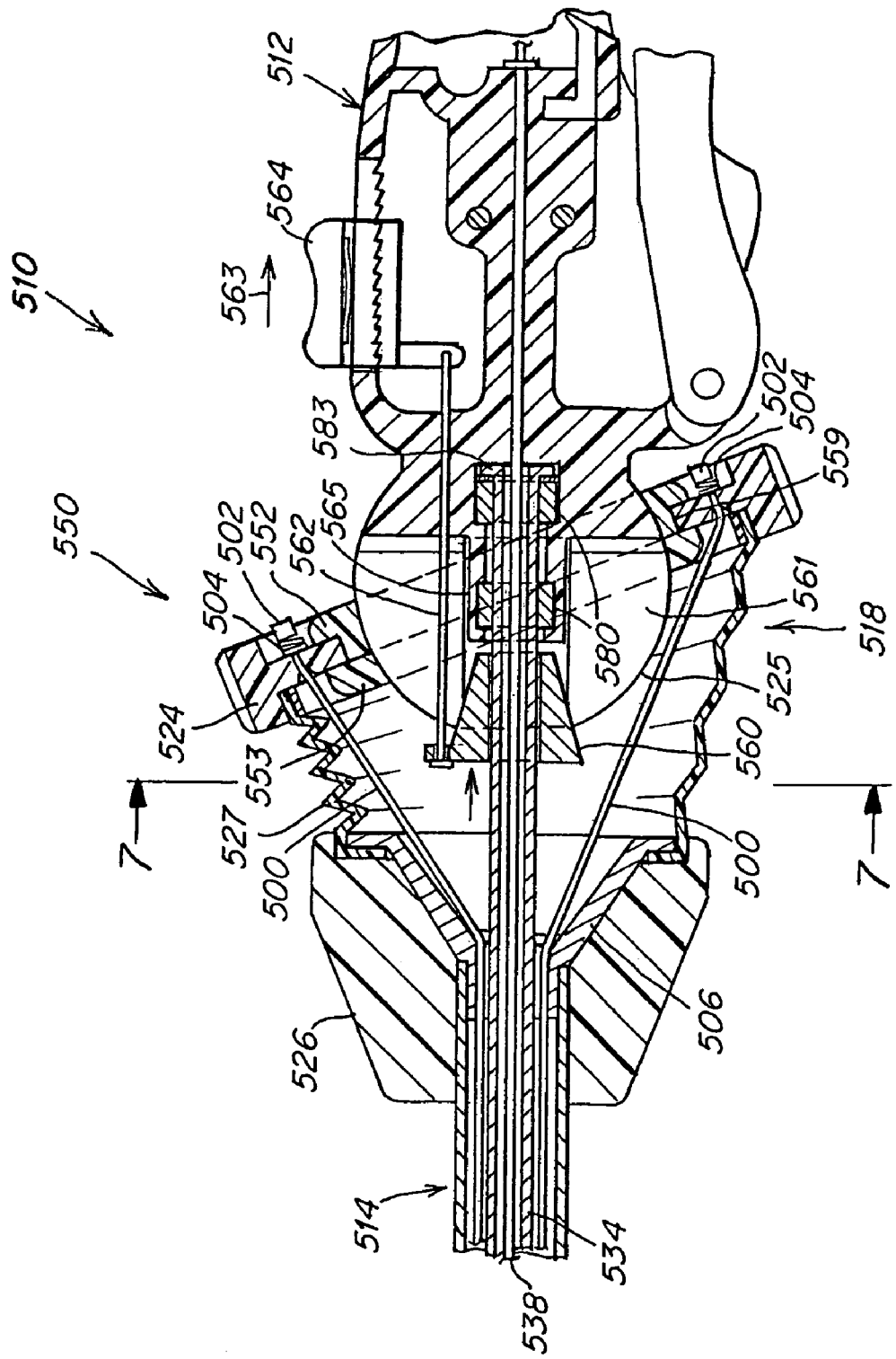
FIG. 6 is a fragmentary cross-sectional view of a further alternate embodiment of the instrument of the present invention as taken at the proximal bendable member.
Figure 7:
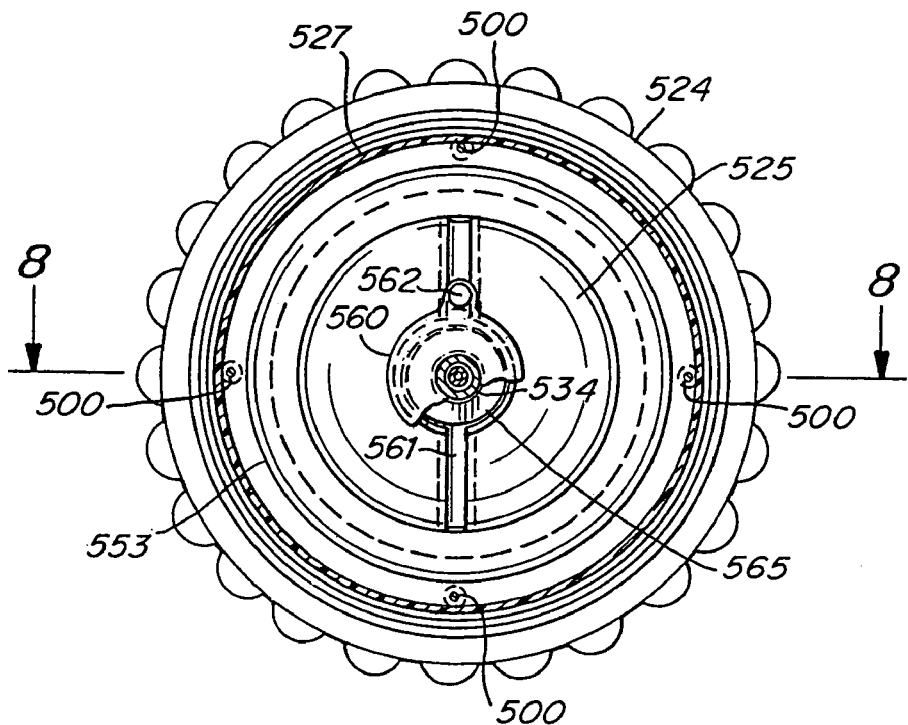
FIG. 7 is a cross-sectional view taken along line 7-7 of FIG. 6.
Figure 8:
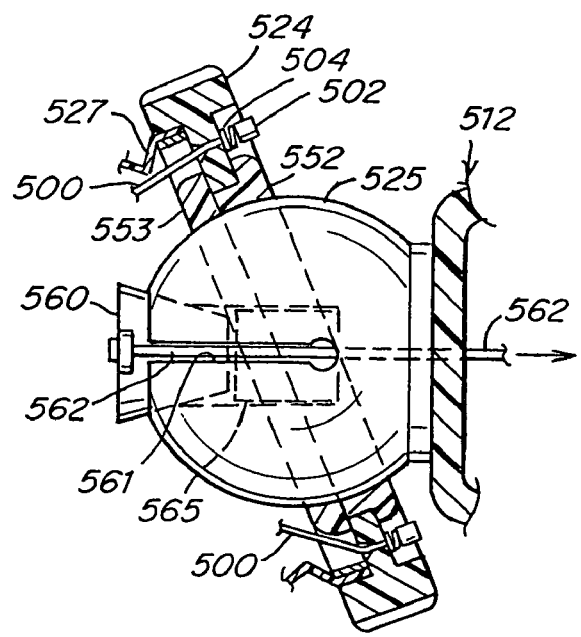
FIG. 8 is a cross-sectional view taken along line 8-8 of FIG. 7.

Reference is now made to FIGS. 6-8 for a still further embodiment of the present invention with a locking mechanism used to lock the position of the proximal and distal bendable members. In FIGS. 6-8, the distal end of the instrument may be the same as described in FIG. 5. In the previous embodiments described herein, the locking member is embodied in the rider and thus the locking occurs by a pressure on the outside of the ball. This is the case in the embodiment where the ball forms part of the handle (FIG. 2) or where the ball is supported separately and from the instrument shaft (FIG. 5). In FIG. 6 the ball is a split ball and a wedge arrangement is used to urge the ball outwardly into engagement with the rider in order to lock the position of the proximal and distal bendable members.

FIGS. 6-8 show the proximal end of the instrument and in particular the proximal bendable member 518 and the related locking mechanism. The surgical instrument 510 is comprised of a handle 512 at the proximal end of the instrument, an elongated instrument shaft 514, only partially shown in FIG. 6, and a tool or end effector disposed at the distal end of the surgical instrument. The instrument shaft and distal end of the instrument in this embodiment may be substantially identical to the embodiment illustrated in FIGS. 1 and 2. The embodiment of FIG. 6 also includes an adaptor cover 526 for partially retaining a portion of the proximal bendable member 518. At the distal end of the instrument shaft there is provided a distal motion or bendable member not shown in FIGS. 6-8.

In the embodiment of the invention depicted in FIGS. 6-8 the ball 525 is integrally formed with the handle 512, similar to that described in FIG. 2. However, in the embodiment of FIG. 2 the ball is a substantially solid ball, whereas in the embodiment of FIG. 6 the ball is a split ball having a split or slot at 561. The handle 512 also includes a shaft support post 565 that supports the bearings 580. As illustrated in FIG. 6 there are actually a pair of bearings 580 with the more proximal one captured by the end collar 583. These bearings and the shaft support post 565 support the inner shaft 534. The inner shaft 534 carries the tool actuation cable 538.

The proximal bendable member 518 is constructed primarily of a bellows 527 that functions with the rotation knob 524 and the rider 552 to control the distal end of the instrument. The bellows 527 is attached at opposite ends to the adaptor 526 at member 506 and also at the rotation knob 524. The ends of the bellows may be secured by a compression fit with the respective adaptor 526 and rotation knob 524. As in the previous embodiments described herein, the bellows is constructed as an accordion pleat and has a relatively rigid construction so that the pleats are relatively stiff in the rotational direction, and yet are readily flexible or foldable in the longitudinal shaft direction.

In all the embodiments that use a bellows, such as the bellows 327 in FIG. 2 or the bellows 527 in FIG. 6, it is noted that the bellows itself functions as a torque transmission means. In other words the bellows have a sufficient rigidity thereto so as to be able to transmit the rotational motion from the rotation knob to the instrument shaft. This may be referred to as the bellows providing rotational torque to distal members such as the instrument shaft and end effector. At the same time the bellows is constructed and arranged to be sufficiently flexible so as to flex (compress or expand) as the bending action is performed. Refer, for example, to FIG. 2 where the bellows 327 is shown flexed to a more open position on the top while flexed to a more closed position at the bottom. Other foldable members may also be used as an alternative to a bellows.

Any rotation imparted to the rotation knob 524 is coupled via the bellows 527 to the adaptor 526 and from there to the instrument shaft 514. This causes the distal end of the instrument to rotate about the tool distal axis. The pitch and yaw of the instrument is also controlled by manipulation of the rider 552. By manipulating at the rotation knob 524, the rider 552 may be tilted such as in the position shown in FIG. 6 to provide a corresponding tilt at the distal end of the instrument. To maintain an interlock between the rider 552 and the rotation knob 524 there is provided a retainer 553 that may be secured to the rider in a well known manner such as with the use of one or more securing fasteners or screws. A raceway is provided between the rotation knob 524 and the rider as indicated at 559. This enables the rotation knob to rotate relative to the rider.

In the embodiment of FIG. 6, the position of the end effector is set by means of the assembly 550 which is considered as including the aforementioned rider 552 and the annular retainer 553. The rider is manipulated via the rotation knob to control the cabling to the end effector and in a pitch and yaw manner. This action pushes and pulls the cabling 500 to set the position of the end effector. At the same time the rotation knob 524 may be rotated to rotate the tip of the instrument about its tip axis. FIG. 6 also shows the cabling 500 and in particular the end lugs 502 and tensioning spring 504.

The embodiment described in FIGS. 6-8 also includes the locking feature that enables the position between the proximal and distal motion members to be fixed at a predetermined position such as at the position illustrated in FIG. 6 where the rotation knob and the rider have been tilted at an angle causing a corresponding positioning oft the tool end of the instrument. Once the surgeon has the instrument in the desired position the locking mechanism is used to conveniently hold the instrument in that position. The specific locking member in FIG. 6 comprises a locking wedge 560 that is adapted to mate with the ball 525 and when the wedge 560 is urged into the ball the slot 561 is spread causing the outer surface of the ball 525 to engage the inner surface of the rider and retainer.

The locking wedge 560 is actuated from the pull rod 562 which in turn is connected at its opposite end to the slide button 564. The slide button 564 may include a tooth ratchet arrangement with a leaf spring which can be used to release the button after it has been slid and engaged. The button 564 is arranged for longitudinal motion in the direction of arrow 563 within the opening 566 in the handle 512. A movement by the operator of the instrument in the direction of arrow 563 causes the push rod 562 to move to the right and this, in turn, causes the wedge 560 to pass more firmly into the slot in the ball 525 thus locking the position of the rider relative to the ball. Even in this locked position, the rotation knob 524 may still be rotated relative to the locked rider 552.

Reference is now made to FIGS. 9-12 for an illustration of a further embodiment of a medical instrument in accordance with the present invention. This instrument includes cabling for controlling the distal bendable member from the proximal bendable member and also includes additional cabling at the proximal bendable member for controlling a means for locking the bendable members in a fixed relationship. This illustrated embodiment uses uni-body structures at both bendable ends of the instrument.

In the embodiment of FIGS. 9-12 the surgical instrument 610 is comprised of a handle 612 at the proximal end of the instrument, an elongated instrument shaft 614 and a tool or end effector 616 that is disposed at the distal end of the surgical instrument. The surgical instrument shaft is usually rigid for laparoscopic procedures, typically constructed of a metal material. For intraluminal procedures the instrument shaft may be at least partially flexible or bendable. FIGS. 9 and 10 are similar schematic cross-sectional views taken 45 degrees apart to illustrate both bending cables 600 as well as locking cables 660.

Figures 10A, 10B:
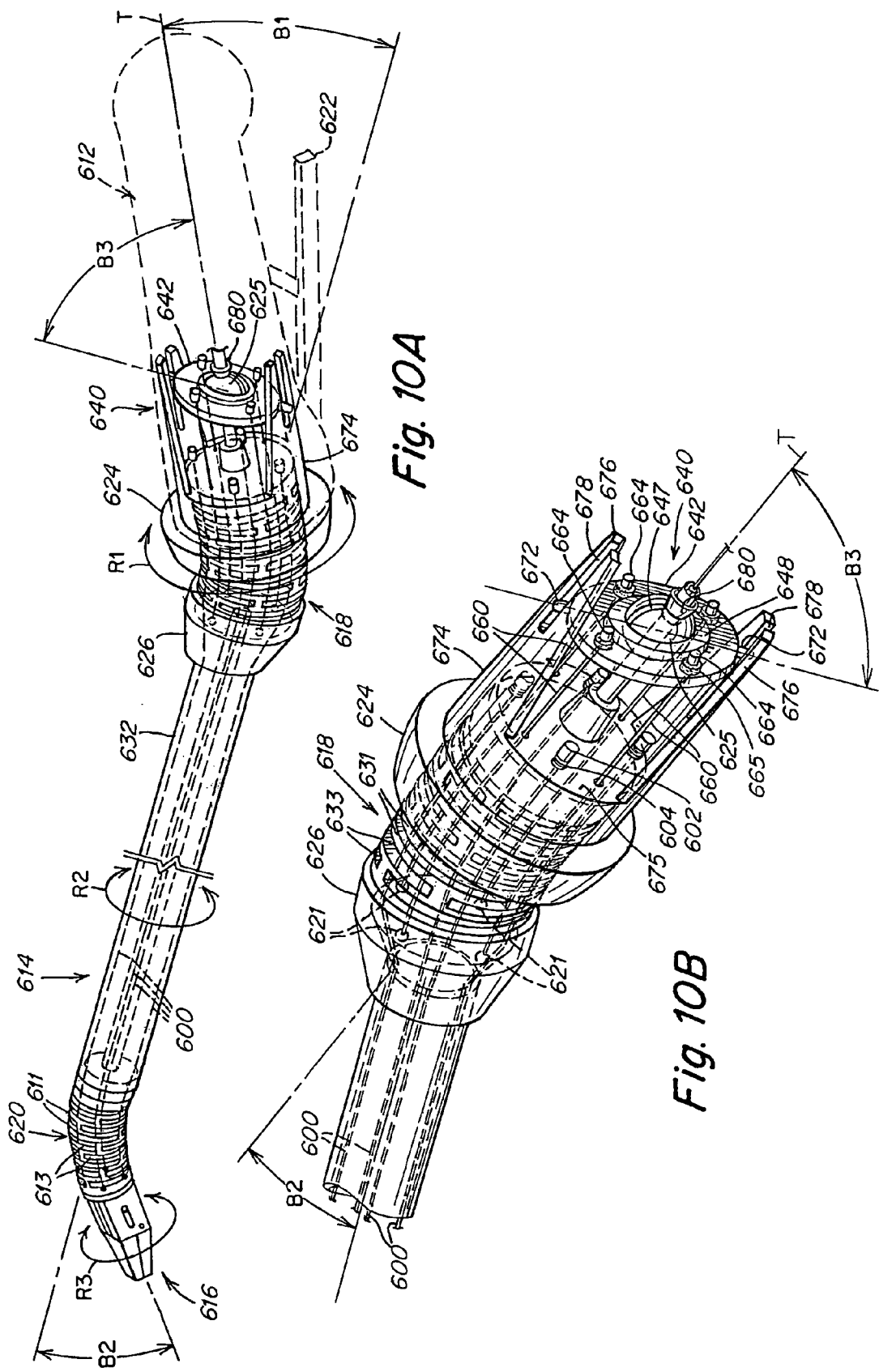
FIG. 10A is a schematic perspective view of the embodiment shown in FIGS. 9 and 10.
FIG. 10B is an enlarged fragmentary perspective view of the embodiment shown in FIGS. 9 and 10 illustrating further details of the locking mechanism but with the handle bent in the opposite direction.
Figure 11:
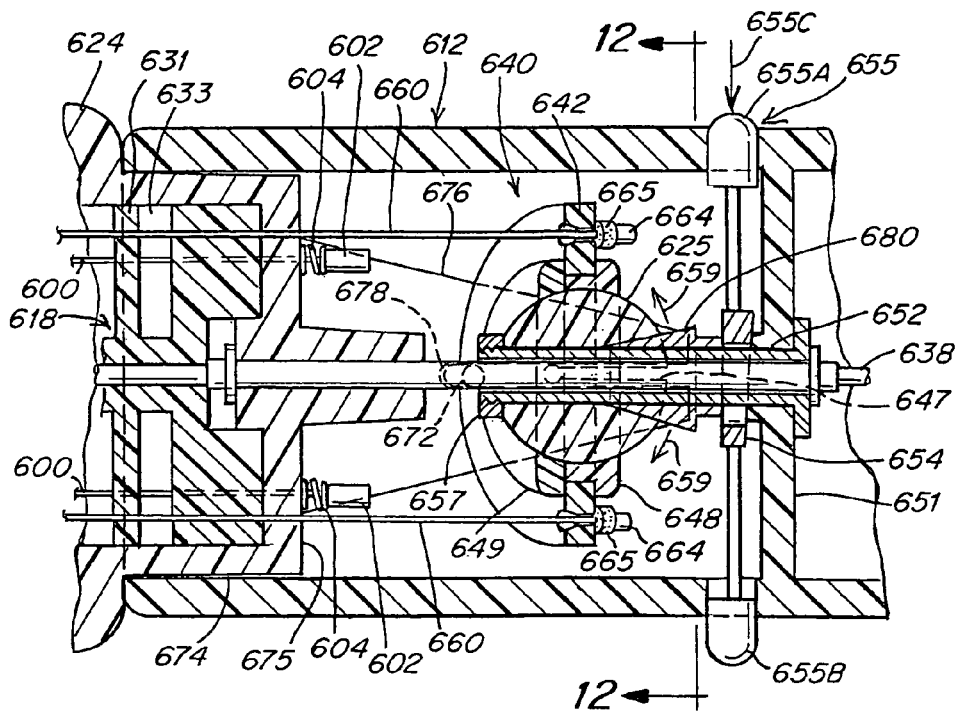
FIG. 11 is a fragmentary schematic cross-sectional plan view of the embodiment of FIGS. 9 and 10 as taken along line 11-11 of FIG. 10.
Figure 12:
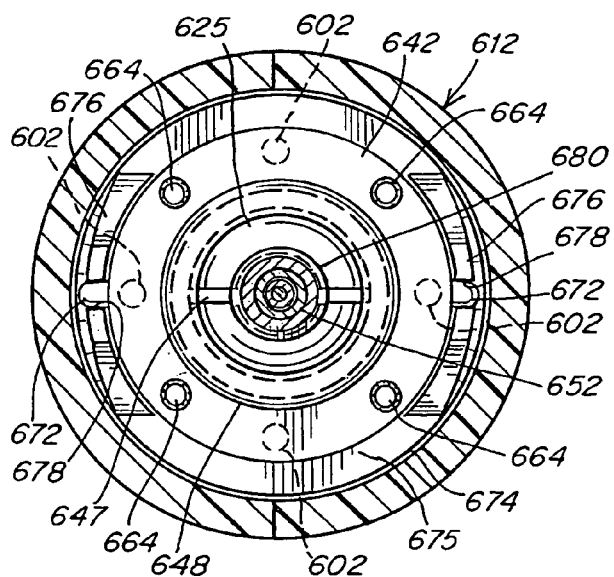
FIG. 12 is a cross-sectional schematic view taken along line 12-12 of FIG. 11.
Figure 12A:
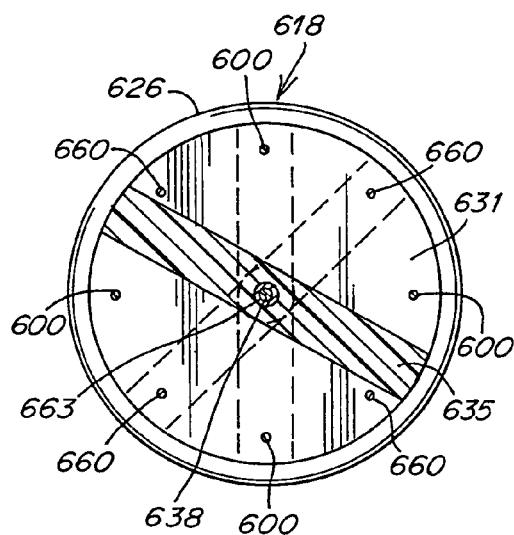
FIG. 12A is a cross-sectional view taken along line 12A-12A of FIG. 10.

FIG. 10A is a schematic perspective view of the embodiment shown in FIGS. 9 and 10. FIG. 10B is an enlarged fragmentary perspective view illustrating further details of the locking mechanism but with the handle bent in the opposite direction. FIG. 11 is a fragmentary cross-sectional plan view taken along line 11-11 of FIG. 10. FIG. 12 is a schematic cross-sectional view taken along line 12-12 of FIG. 11. FIG. 12A is a cross-sectional view along line 12A-12A of FIG. 10.

In this embodiment, the handle 612 may be comprised of two handle halves. A lever 622 (see FIG. 10A) is manipulated by the surgeon for opening and closing the end effector 616 at the distal end of the instrument shaft 614. The end effector 618 is comprised of a movable jaw 644 and a fixed jaw 646. The rotation knob 624 at the proximal end of the instrument shaft is used to rotate the entire instrument shaft and end effector. This rotation is illustrated in FIG. 10A by the circular arrows R1, R2 and R3. An adaptor cover 626 partially retains a portion of the proximal bendable member 618 as shown in FIGS. 9 and 10.

At the distal end of the instrument shaft 614, there is provided the distal bendable member 620. The distal bendable member 620 may be covered by a thin plastic sheath or tube to protect the distal bendable member. Both the distal and proximal bendable members are preferably constructed of a plastic material.

In the schematic diagram of FIG. 10A the end effector 616 may be considered as disposed at an operative site. This diagram also depicts the rolling motion that can be performed with the instrument of the present invention. This occurs by virtue of the rotation of the rotation knob 624 relative to the handle 612. This is illustrated by the circular rotation arrow R1 in FIG. 10A. When the rotation knob 624 is rotated in either direction this causes a corresponding rotation of the instrument shaft 614. This is depicted in FIG. 10A by the rotational arrow R2. This same motion also causes a rotation of the end effector 616 about the tip longitudinal axis, as illustrated by the rotational arrow R3.

As indicated previously, the end effector or tool 616 is actuated by means of a jaw actuation member including the elongated lever 622. The lever 622 is supported from the handle housing. This operates the tool actuator cable 638 from a slider (not shown) in the handle housing. When the cable 638 is moved to the right, then the jaws are moved toward a closed position. In FIG. 9 the jaws are illustrated as closed grasping a needle 645.

The instrument shaft 614 includes an outer shaft tube 632 that may be constructed of a lightweight metal material or may be a plastic material. The proximal end of the tube 632 is received by the adaptor cover 626. The distal end of the tube 632 is secured to the distal bendable member 620. The distal bendable member 620 as illustrated in FIGS. 9 and 10 is a uni-body or unitary structure and is comprised of a series of discs 611 defining therebetween slots 613. Within the outer shaft tube 632 there is provided a support tube 634 that is preferably constructed of a plastic material. Tube 634 extends between the distal bendable member 620 and the proximal bendable member 618. The jaw actuator cable 638 extends within this support tube 634. The support tube 634 may have disposed along its length a series of spacers 505. Each of the spacers is preferably evenly spaced along the instrument shaft and may be provided with slots for accommodating the tool actuator cables.

FIGS. 9 and 10 also illustrate the bending control cables 600 extending through the distal bendable member 620. The terminating ends of the cables 600 connect to anchors 656 for respective control cables. The jaw actuator cable 638 terminates at its distal end at the end effector. Within each of the bendable sections or bendable members 618 and 620 there is provided a plastic tube. This includes a distal tube 661 and a proximal tube 663. Both of these tubes may be constructed of a plastic such as polyethyletherkeytone (PEEK). The material of the tubes is sufficiently rigid to retain the cable and yet is flexible enough so that it can readily bend with the bending of the bendable members. The tubes are longitudinally stiff, but laterally flexible.

As indicated previously, the control between the proximal bendable member 618 and the distal bendable member 620 is carried out by means of the flex control cables 600. There are four such cables. At the distal end of these cables, as mentioned before, the cables connected to anchors 656 at the jaw end of the instrument. The cables 600 are retained at there proximal ends by cable end lugs 602 terminating at the proximal end of the proximal member. Preferably springs 604 or other resilient members are retained between these end lugs 602 and a wall of the rotation knob 624. The springs 604 tension or take up the slack on the cables. Within the adaptor cover 626, the cables 600 extend through the transition member 606. The cables then extend to a larger diameter outer locus as they extend through the proximal bendable member. The stepped transition member 606 may be of metal and is secured to the end of the tube 632.

The proximal bendable member 618 is constructed in a similar manner to the distal bendable member 620 but is preferably of a larger diameter. Both of these members are in the form of a single piece uni-body slotted structure comprised of alternating slots and discs. The discs are supported from a central member. FIGS. 9 and 10 illustrate the discs 631 defining therebetween the slots 633. These discs are provided with holes for receiving the bend control cables as well as the cables associated with the locking mechanism, to be described hereinafter. These proximal and distal bendable members may also be preferably provided with transverse ribs.

In previous embodiments described herein, the locking of the instrument has occurred primarily by means of locking the rider for the rotation knob. This locking has occurred by way of either locking levers or a locking wedge arrangement. In the embodiment of the invention illustrated in FIGS. 9-12 the locking occurs by means of the use of a separate follower member illustrated as locking mechanism 640. This follower mechanism operates in conjunction with lock cables 660 to lock a particular position of the proximal bendable member, and by doing so also locking the position of the distal bendable member, as the proximal and distal bendable members are interconnected by actuation cables 600.

The locking mechanism 640 includes, inter alia, an anchor ring 642 that provides the primary support for the locking cables 660, as well as the support of the locking mechanism from the rotation knob structure. In this regard, the anchor ring 642 includes diametrically disposed pins 672 that are accommodated in elongated slots 678 of the opposed rearwardly extending fingers 676. Refer in particular to FIGS. 10B and 11. The fingers 676 extend from the rotation knob barrel 674. As illustrated in FIG. 11, the end wall 675 of the barrel 674 supports the proximal end of the bending cables 600. The cables 660 are relatively rigid and generally of a larger diameter than the cables 600. All of the cables 600 are preferably of the same length.

When the instrument illustrated in this embodiment is in a straight in-line position then the locking mechanism, and particularly the anchor ring 642 extends substantially transverse to the center axis. When the handle 612 is bent, such as in the positions shown in FIGS. 9 and 10 then it is noted that the follower locking mechanism 640 tilts relative to the longitudinal axis T. When it is desired to lock the mechanism in a particular bent condition then the wedge member 680 engages the split ball 625 and this locks the position of the anchor ring 642 and thus also locks the position of the locking or anchor cables 660. This, in turn, locks the position of the proximal bendable member 618 and via the cables 600 also locks the position of the distal bendable member 620. The rigidity of the locking cables 660 maintains the proximal bendable member 618 in the locked position.

Each of the cables 660 are disposed 90 degrees apart, as are the bent cables 600. Refer to FIG. 12A for an illustration of the placement of these cables. It is noted that the cables 660 are disposed 45 degrees to the cables 600. This 45 degree different position is illustrated in respective FIGS. 9 and 10. The distal end of each cable 660 terminates at lug end 621. As indicated previously, the proximal end of each cable 660 terminates at lug 664 and spring or resilient member 665. Rotation of the rotation knob 624 causes rotation of the entire proximal bendable member and the locking mechanism 640.

The locking mechanism 640 includes, in addition to the anchor ring 642, the rider 648 and the retaining ring 649. Fastening screws or the like are used for securing together the rider 648 and the retaining ring 649 about the spherical ball 625 as illustrated in FIG. 11. The ball 625 is also supported at its center by means of the sleeve 652 that has a flange on one end adjacent to the wall 651 and a securing nut 657 at the opposite end. The wedge member 680 is adapted to slide on the sleeve 652 into the slit 647 in the spherical ball 625. The cross-sectional view of FIG. 12 illustrates the ball 625 with its slit 647. FIG. 12 also illustrates the wedge member 680 in cross-section.

The conical wedge 680 is moved by means of a button arrangement that includes the lock button 655. This button may be considered as having opposite ends 655A and 655B. When the button end 655A is moved in the direction of arrow 655C then this locks the position of the instrument. When, instead, the button end 655B is depressed toward the handle housing then this releases the locked position.

FIG. 9 is a cross-sectional view of the instrument of this embodiment with the handle bent at an angle B1 which causes a corresponding bending at the distal end of the instrument at an angle B2 to the longitudinal shaft axis. In this embodiment the instrument can also be controlled in any direction including directions in and out of the plane of the paper in FIG. 9. In FIG. 9 it is noted that the handle is bent downwardly causing a corresponding bending upwardly of the distal end of the instrument. As indicated previously the cable lengths of the cables 660 are the same and thus when the handle is bent in the manner illustrated in FIG. 9 the locking mechanism 640 tilts and essentially follows the positioning of the proximal bendable member. The locking mechanism 640 has the ability to tilt at any angle and moreover, by virtue of the pins 672 in the slots 678, the locking mechanism 640 may also pivot relative to the rotation knob by transitioning in the elongated slots 678.

The cross-sectional view of FIG. 10 is similar to that described in FIG. 9 but with the rotation knob 624 rotated through 45 degrees. Thus, this illustrates the support fingers 676 and the associated elongated slots 678 for the pins 672. FIG. 10 also illustrates the locking cables 660 with their terminations at 621 and 664. A resilient member 665 is preferably provided, as shown in FIG. 11, between the termination 664 and the anchor ring 642.

FIG. 10A illustrates the same instrument illustrated in FIGS. 9 and 10 but with the handle now tilted upwardly so as to provide a corresponding downward tilting at the distal end of the instrument. It is also to be noted from FIG. 10A that, with this direction of the handle, the follower mechanism 640 tilts in the opposite direction to that illustrated in FIGS. 9 and 10. The fragmentary view of FIG. 10B illustrates substantially the same tilt of the locking mechanism 640 as illustrated in FIGS. 9 and 10. In FIG. 10B the handle has been moved downwardly in the direction illustrated at an angle B1.

FIG. 11 is a cross-sectional view taken along line 11-11 of FIG. 10. This illustrates the sliding wedge 654 that is used to transition the cone 680 into the split ball 625. This action locks the ball 625 relative to the rider 648. FIG. 11 illustrates the lock mechanism 640 in its locked position with the slide wedge 654 having been moved downwardly to transition (force) the conical wedge member to the left in FIG. 11. This urges the split of the ball apart in the direction of arrows 659 to urge the outer surfaces of the spherical ball against the rider 648 and the associated retaining ring 649. In the view of FIG. 11 it is also noted that the anchor ring 642 is illustrated as tilted forward at the back side. FIGS. 12 and 12A are additional cross-sectional views that illustrate the instrument.

In the embodiments of the present invention illustrated herein, the locking member has been in the form of a pivotal lever. However, various other types of locking members may be employed. These locking members are preferably mounted on the handle or close to the handle so that they are in easy reach of the user of the instrument. The locking member is also preferably manually controllable so as to be in either a released position or an activated or locked position.

Another aspect of the surgical instrument of the present invention is the ability to adapt the instrument to a wide variety of medical procedure. This includes, but is not limited to, access to a body cavity such as through an incision or intraluminal use such as through a natural body aperture to a body lumen. The introduction of the surgical instrument into the anatomy may also be by percutaneous or surgical access to a lumen, cavity or vessel, or by introduction through a natural orifice in the anatomy.

In accordance with still other embodiments of the present invention the bendable members that have been illustrated as uni-body structures (see, for example, FIGS. 2 and 9) can, alternatively, be constructed and arranged as ball and socket joints or a series of engageable discs, such as illustrated in co-pending provisional application Ser. No. 60/802,885 filed on May 23, 2006, shown in FIG. 6, 10 or 13 and which is hereby incorporated by reference in its entirety.

There are several improvements brought forth by employing bendable sections for the motion members particularly as opposed to other mechanisms such as pivotal joints or ball-and-socket joints.

A first important attribute of a bendable member is in its inherent lateral (bending) stiffness, especially when used for the proximal handle motion member. In a jointed arrangement the proximal joint is situated between the elongated shaft and the control handle, together with the fulcrum at the incision. This behaves as a "double-joint" and the instrument may have a serious tool stability issue if the joint is "free" to move. Suppose the operating surgeon slightly moves his/her wrist while holding the control handle of the instrument. If the joint is "free" to move without providing substantial support resistance, due to the fulcrum effect of the long elongated shaft passing through the incision, it will result in substantial, unintended swinging of the tool end of the instrument in opposite direction. In a typical laparoscopic or endoscopic procedure where the operating field is small, such instability of the tool will render the tool potentially dangerous and unusable. Unlike the pivotal or ball-and-socket joints that are "free" to move, a bendable member has inherent stiffness which acts to provide necessary support for stabilizing the operator hand's wrist movement, which in turn stabilizes the tool motion. By varying the material and geometry of the bendable member, the appropriate level of stability could be selected.

A second important attribute of the bendable member, especially for bending in two degrees of freedom, is its uniformity in bending. Because the bendable member can bend in any direction uniformly, it has no inherent singularity, and as the result, the operator can produce uniform rolling motion of the tool, an important motion for tasks such as suturing, simply by rolling the control handle. On the other hand, if the motion members are comprised of series of pivotal joints, not only may it bind due to singularities, but the rolling of the control handle will result in unwanted side motion of the tool as well, affecting its usability for surgical procedure.

A third attribute of the bendable member is its ability to transmit substantial torque axially. By selecting appropriate material and geometry, the bendable member can be constructed to transmit torque axially necessary to perform surgical procedure. On the other hand, the motion member comprised of ball-and-socket joints will not be able to transmit the necessary torque from the handle to the tool end.

A fourth attribute of the bendable member is that it has no sharp bending point, location or pivot and thus this results in an increased life and higher performance. Either pivotal or ball-and-socket joints on the other hand have sharp corners which can increase friction, reduce life and decrease performance of the tool actuation push rod passing through.

A fifth attribute of the bendable member is in the reduction of manufacturing cost. The bendable motion member can be injection molded as a single body, thus significantly reducing the cost. Pivotal or ball-and-socket joints are comprised of more parts and this results in a higher manufacturing cost.

Lastly, a sixth attribute of the bendable member is that it can be easily customized. By varying the stiffness at different points of the bendable member, one can optimize its bending shape for specific applications.

While this invention has been particularly shown and described with references to preferred embodiments thereof, it will be understood by those skilled in the art that various changes in form and details may be made therein without departing from the scope of the invention encompassed by the appended claims. For example, the embodiments described herein have primarily used four control cables for providing all direction motion of the motion members. In alternate embodiments fewer or greater numbers of cables may be provided. In a most simplified version only two cables are used to provide single DOF action at the bendable motion member. Also, the disclosed embodiment uses a handle that is essentially in line with the instrument shaft. In an alternate embodiment of the invention the handle can be off axis or at an angle to the instrument shaft in the rest position of the instrument. In the illustrated embodiments a rotation knob has been used to perform the function of rotating the distal instrument tip. In an alternate embodiment of the invention other means may be provided to accomplish such tip rotation. For example, a slide member may be used in place of a rotation knob, or any other moveable member that controls the instrument shaft and instrument tip for rotation of the end effector about a distal tool axis such as shown in FIG. 3 (axis P).

What is claimed is:

1. A medical instrument comprising:
    a handle;
    a distal work member;
    a proximal movable member controlled from said handle;
    a distal movable member controlled from said proximal movable member to provide controlled movement of said distal work member;
    an instrument shaft that intercouples said proximal and distal movable members;
    and actuation means coupled between said movable members;
    said handle having a ball end with an outer at least partially spherical surface;
    said proximal movable member comprising a movable ring assembly supported about the ball end of said handle and adapted for multi-directional motion relative to the ball end of said handle;
    said movable ring assembly including an annular rider having an inner concave surface that rides on and conforms to the outer at least partially spherical surface of the ball end;
    said annular rider constructed and arranged for the multi-directional motion over the outer spherical surface of the ball end to, in turn, control multi-directional motion of said distal movable member;
    wherein said actuation means comprises a set of cables, each having proximal and distal cable ends that couple between said movable members and further including a rotation knob coupled with the rider while rotationally mounted relative to the rider and a cable retainer supported by said rotation knob and for retaining proximal ends of said cables.

2. The medical instrument of claim 1 wherein said cable retainer is an annular cable retainer and further including a locking member mounted on said annular rider and having locked and unlocked states; said locking member in said unlocked state enabling control of said distal work member via said movable members; and said locking member, in said locked state, holding said movable members in a desired fixed position.

3. The medical instrument of claim 2 wherein said locking member, in the locked state, fixes the position of the proximal movable member by locking the annular rider to the ball end.

4. The medical instrument of claim 1 wherein said distal movable member comprises a uni-body structure.

5. The medical instrument of claim 1 wherein said rotation knob controls said distal work member to rotate about a distal work member longitudinal axis.

6. The medical instrument of claim 5 wherein said rotation knob comprises an annular rotation knob that is coupled with the rider while rotationally mounted relative to the rider.

7. The medical instrument of claim 1 wherein said movable ring assembly further comprises a locking member mounted on said rider, having locked and unlocked states and for engagement with the ball end in the locked state.

8. The medical instrument of claim 1 wherein the proximal movable member also includes an outer bellows having proximal and distal ends with the proximal end thereof attached to the rotation knob for rotation therewith, said outer bellows constructed and arranged to provide torque transmission to the distal work member while providing axial compression and expansion to facilitate a bending action between the movable members.

9. The medical instrument of claim 1 wherein said ball end has a split to receive a locking wedge to lock the position of the rider on the ball end.

10. The medical instrument of claim 9 including a slide button mounted on the handle for controlling said locking wedge position relative to said ball end.

11. The medical instrument of claim 1 wherein said instrument shaft has proximal and distal ends and further including bearing means in the ball end for rotational support of the proximal end of the instrument shaft.

12. A medical instrument comprising:
a handle;
a distal work member;
a proximal movable member controlled from said handle;
a distal movable member controlled from said proximal movable member to provide controlled movement of said distal work member;
an instrument shaft that intercouples said proximal and distal movable members;
actuation means coupled between said movable members;
said handle having a ball end with an outer at least partially spherical surface;
said proximal movable member comprising a movable ring assembly supported about the ball end of said handle and adapted for multi-directional motion relative to the ball end of said handle;
said movable ring assembly including an annular rider having an inner concave surface that rides on and conforms to the outer at least partially spherical surface of the ball end;
said annular rider constructed and arranged for the multi-directional motion over the outer spherical surface of the ball end to, in turn, control multi-directional motion of said distal movable member;
wherein said movable ring assembly includes a rotation control member for controlling said distal work member to rotate about a distal work member axis;
wherein said rotation control member comprises an annular rotation knob that is coupled with the rider while rotationally mounted relative to the rider; and
a bearing means between the annular rotation knob and the rider and a locking lever mounted on the rider, having locked and unlocked states and for engagement with the ball end in the locked state.

13. The medical instrument of claim 12 wherein said actuation means comprises a set of cables, each having proximal and distal cable ends, and that couple between said movable members and further including a cable retainer supported by said rotation knob and for retaining proximal ends of said cables.

14. The medical instrument of claim 12 wherein the actuation means comprises a set of control cables, each having proximal and distal ends, and further including means for mounting the proximal ends of the cables at the annular rotation knob.

15. The medical instrument of claim 14 wherein said means for mounting includes a separate cable retainer that is secured with and rotates with the rotation knob.

16. The medical instrument of claim 15 wherein said locking lever is mounted on said rider and has a pad means for engagement with the outer at least partially spherical surface of the ball end.

17. The medical instrument of claim 12 wherein said actuation means comprises cables and said rotation knob also includes a cable retainer for retaining the proximal ends of the cables, and further including bearing means supported in the ball end for rotational support of the instrument shaft.

18. A medical instrument comprising:
a handle;
a distal tool;
a proximal movable member controlled from said handle;
a distal movable member controlled from said proximal movable member to provide controlled movement of said distal tool;
an instrument shaft that intercouples said proximal and distal movable members;
and actuation means coupled between said movable members and including at least a first cable set disposed between the proximal and distal movable members so that any movement of the proximal movable member causes a corresponding movement of the distal movable member;
a ball means supported by one of the instrument shaft and handle;
said ball means having an outer at least partially spherical surface;
an annular rider having an inner concave surface that rides on and conforms to the outer at least partially spherical surface of the ball means;
said annular rider constructed and arranged for motion over the outer at least partially spherical surface of the ball member based on relative motion therebetween;
and a locking member associated with the ball means for fixing the position of the rider on the ball means to thereby freeze the relative position between the proximal and distal movable members;
wherein said first cable set has proximal and distal cable ends that couple between said movable members and further including a rotation knob coupled with the rider while rotationally mounted relative to the rider and a cable retainer supported by said rotation knob and for retaining proximal ends of said cables.

19. The medical instrument of claim 18 wherein said said proximal and distal movable members are bendable members.

20. The medical instrument of claim 18 including a bearing means between the rotation knob and the rider and a locking lever mounted on the rider, having locked and unlocked states and for engagement with the ball means in the locked state.

21. A medical instrument comprising:
a handle;

a distal tool;
a proximal movable member controlled from said handle;
a distal movable member controlled from said proximal movable member to provide controlled movement of said distal tool;
an instrument shaft that intercouples said proximal and distal movable members;
and actuation means coupled between said movable members and including at least a first cable set disposed between the proximal and distal movable members so that any movement of the proximal movable member causes a corresponding movement of the distal movable member;
a ball means supported by one of the instrument shaft and handle;
said ball means having an outer at least partially spherical surface;
an annular rider having an inner concave surface that rides on and conforms to the outer at least partially spherical surface of the ball means;
said annular rider constructed and arranged for motion over the outer at least partially spherical surface of the ball member based on relative motion therebetween;
a locking member comprising a locking lever; wherein the locking member is associated with the ball means for fixing the position of the rider on the ball means to thereby freeze the relative position between the proximal and distal movable members;
a rotation knob for controlling said distal tool to rotate about a distal tool axis, the rotation knob being coupled with the rider while rotationally mounted relative to the rider;
a bearing means between the rotation knob and the rider, and the locking lever being mounted on the rider, the locking lever having locked and unlocked states and for engagement with the ball means in the locked state.

22. The medical instrument of claim 21 wherein said proximal and distal movable members comprise bendable members.

23. A medical instrument comprising:
a handle;
a distal tool;
a proximal movable member controlled from said handle;
a distal movable member controlled from said proximal movable member to provide controlled movement of said distal tool;
an instrument shaft that intercouples said proximal and distal movable members;
and actuation means coupled between said movable members and including a set of cables, each cable of the set having proximal and distal cable ends, and coupled between the proximal and distal movable members so that any movement of the proximal movable member causes a corresponding movement of the distal movable member;
a ball supported by one of the instrument shaft and handle;
said ball having an outer at least partially spherical surface;
a movable ring assembly including a rider having an inner concave surface that rides on and conforms to the outer at least partially spherical surface of the ball;
a rotation knob coupled with the rider while rotationally mounted relative to the rider;
said movable ring assembly further including a cable retainer supported by said rotation knob and for retaining the proximal ends of said cables.

24. The medical instrument of claim 23 wherein said cable retainer comprises an annular cable retainer that is supported by said rotation knob for rotation therewith and that is for retaining proximal ends of said cables.

25. The medical instrument of claim 24 including a locking member associated with the ball for fixing the position of the rider on the ball to thereby freeze the relative position between the proximal and distal movable members.

26. The medical instrument of claim 23 including a locking mechanism associated with the ball for fixing the position of the rider on the ball to thereby freeze the relative position between the proximal and distal movable members.

27. The medical instrument of claim 26 wherein the locking mechanism includes a locking lever mounted on the rider, having locked and unlocked states and for engagement with the ball in the locked state.

28. The medical instrument of claim 27 wherein the locking lever includes a pad means for engagement with the outer at least partially spherical surface of the ball.

29. The medical instrument of claim 23 wherein the handle is maintained in line with the instrument shaft, and the rotation knob is manipulated to both rotate relative to the ball, as well as to move on the ball in any direction.

30. The medical instrument of claim 23 wherein the ball is attached to a proximal end of the instrument shaft and the rider is formed integral with the handle.

31. The medical instrument of claim 23 wherein the ball is formed with the handle and the movable members are bendable members.

32. The medical instrument of claim 31 including bearing means supported in the ball for rotational support of the instrument shaft.

33. The medical instrument of claim 23 wherein the proximal movable member includes a bellows having proximal and distal ends with the proximal end thereof attached to the rotation knob for rotation therewith, said bellows constructed and arranged to provide torque transmission to the distal tool while providing axial compression and expansion to facilitate a bending action between the movable members.

34. The medical instrument of claim 23 wherein the movable members are bendable members.

35. The medical instrument of claim 23 including bearing means disposed between the rotation knob and the rider.

36. The medical instrument of claim 23 wherein the rider is integrally formed with the handle and further including a locking mechanism carried by the rider.

37. The medical instrument of claim 36 including a locking lever mounted on the rider, having locked and unlocked states and for engagement with the ball in the locked state.

38. The medical instrument of claim 36 wherein the ball is attached to a proximal end of the instrument shaft and the handle bends or deflects at the rider relative to the ball.

39. The medical instrument of claim 38 wherein the locking mechanism includes a locking lever mounted on the rider, having locked and unlocked states and for engagement with the ball in the locked state.

40. The medical instrument of claim 23 wherein the ball is integrally formed with the handle, the handle is maintained in line with the instrument shaft, and the rotation knob and rider are manipulated to both rotate relative to the ball, as well as to move on the bail in any direction.

41. The medical instrument of claim 40 including bearing means supported in the ball for rotational support of the proximal end of the instrument shaft.

42. The medical instrument of claim 40 including a locking mechanism carried by the rider.

* * * * *